(12) United States Patent
Rusinek et al.

(10) Patent No.: US 8,280,482 B2
(45) Date of Patent: Oct. 2, 2012

(54) METHOD AND APPARATUS FOR EVALUATING REGIONAL CHANGES IN THREE-DIMENSIONAL TOMOGRAPHIC IMAGES

(75) Inventors: Henry Rusinek, Great Neck, NY (US); Mony J. De Leon, New York, NY (US)

(73) Assignee: New York University, New York, NY (US)

( * ) Notice: Subject to any disclaimer, the term of this patent is extended or adjusted under 35 U.S.C. 154(b) by 1330 days.

(21) Appl. No.: 11/109,340

(22) Filed: Apr. 19, 2005

(65) Prior Publication Data

US 2005/0244036 A1 Nov. 3, 2005

Related U.S. Application Data

(60) Provisional application No. 60/563,336, filed on Apr. 19, 2004, provisional application No. 60/623,840, filed on Oct. 29, 2004.

(51) Int. Cl.
*A61B 5/05* (2006.01)

(52) U.S. Cl. ............ 600/407; 600/410; 382/128

(58) Field of Classification Search ............ 600/407, 600/476, 443, 410, 447; 382/128, 173
See application file for complete search history.

(56) References Cited

U.S. PATENT DOCUMENTS

| | | | | |
|---|---|---|---|---|
| 4,945,478 A | * | 7/1990 | Merickel et al. | 382/131 |
| 5,583,975 A | * | 12/1996 | Naka et al. | 345/426 |
| 5,664,572 A | * | 9/1997 | Kishimoto | 600/443 |
| 5,887,074 A | * | 3/1999 | Lai et al. | 382/128 |
| 6,236,881 B1 | * | 5/2001 | Zahler et al. | 600/476 |
| 6,254,540 B1 | * | 7/2001 | Kikuchi et al. | 600/443 |
| 6,366,800 B1 | * | 4/2002 | Vining et al. | 600/425 |
| 6,373,568 B1 | * | 4/2002 | Miller et al. | 356/326 |
| 7,027,054 B1 | * | 4/2006 | Cheiky et al. | 345/473 |
| 7,065,235 B2 | * | 6/2006 | Dewaele | 382/132 |
| 7,149,564 B2 | * | 12/2006 | Vining et al. | 600/425 |
| 2002/0033454 A1 | * | 3/2002 | Cheng et al. | 250/339.12 |
| 2002/0050924 A1 | * | 5/2002 | Mahbub | 340/426 |
| 2003/0097069 A1 | * | 5/2003 | Avinash et al. | 600/447 |
| 2003/0135105 A1 | * | 7/2003 | Jack et al. | 600/410 |
| 2007/0064981 A1 | * | 3/2007 | Meijer | 382/128 |

OTHER PUBLICATIONS

WO 9837517 A, Ahn, D K et al., Method of interactively displaying three-dimensional rendering of structure e.g. human lung—involves creating iso-surface of selected region of interest from volume of data based on selected value of physical property representing selected region of interest.*

* cited by examiner

*Primary Examiner* — Brian Casler
*Assistant Examiner* — Nasir Shahrestani
(74) *Attorney, Agent, or Firm* — Dorsey & Whitney LLP

(57) ABSTRACT

Methods for measuring atrophy in a brain region occupied by the hippocampus and entorhinal cortex. In one example, MRI scans and a computational formula are used to measure the medial-temporal lobe region of the brain over a time interval. This region contains the hippocampus and the entorhinal cortex, structures allied with learning and memory. Each year this region of the brain shrank in people who developed memory problems up to six years after their first MRI scan. The method is also applicable for measuring the progression rate of atrophy in the region in an instance where the onset of Alzheimer's disease has already been established.

41 Claims, 10 Drawing Sheets

Graphs show atrophy rate in the MTL (left) and whole brain (right) versus age. O = no cognitive decline, O = decline to MCI, ● = decline to AD.

Graph shows sensitivity of atrophy rate to the position of the MTL region. Estimated error in MTL atrophy rate (vertical axis) for each of 45 brains is obtained by perturbing each coordinate by ±4 mm. The dashed lines indicate the 95% CI.

METHOD AND APPARATUS FOR EVALUATING REGIONAL CHANGES IN THREE-DIMENSIONAL TOMOGRAPHIC IMAGES

RELATED APPLICATIONS

This application claims priority under 35 U.S.C. §119(e) to U.S. provisional patent application Ser. No. 60/563,336, entitled "METHOD FOR EVALUATING REGIONAL BRAIN ATROPHY RATES TO PREDICT FUTURE COGNITIVE DECLINE," filed Apr. 19, 2004, and U.S. provisional application Ser. No. 60/623,840, entitled "System, Software Arrangement and Method for Segmenting an Image," filed on Oct. 29, 2005; the disclosure of each application is hereby incorporated by reference in its entirety.

GOVERNMENT RIGHTS

The reduction to practice of the present invention was in part supported by the U.S. Government under contract awarded by the National Institute of Health, and accordingly the U.S. government may have certain rights in the invention.

FIELD OF INVENTION

This invention relates generally to methods for identifying changes in three-dimensional images acquired by tomographic instruments, and more specifically relates to methods for predicting future cognitive decline and/or for measuring the progression rate of atrophy by examination of brain structure.

BACKGROUND OF INVENTION

Alzheimer's disease is a progressive illness that kills neurons in the brain, initially causing memory loss and eventually leading to dementia. It afflicts some four million older adults in the United States, and perhaps three times as many individuals suffer early-stage forms of the disease that incapacitate memory to one degree or another. Currently, the disease can be diagnosed definitely only after a person dies by an autopsy that shows certain brain abnormalities.

As recognized by the present inventors, brain researchers would like to reliably identify changes in brain structure and metabolism associated with early Alzheimer's disease, before symptoms emerge. Such information would buy precious time when potential therapies could delay or prevent the memory-robbing disease altogether. Furthermore, where the onset of Alzheimer's disease has already been determined, it is of great interest to be able to measure the progression rate of brain atrophy, as recognized by the present inventors.

Research by the present inventors and others have shown that magnetic resonance imaging (MRI) and positron emission tomography (PET) imaging can reveal structural and metabolic changes in the brain that appear to point to early losses in memory and intellectual ability. For example, the present inventors have demonstrated with MRI scans that the hippocampus of the brain shrinks in people with mild cognitive impairment (MCI), a form of memory loss that often precedes Alzheimer's.

Despite the promise of the MRI studies, the hippocampus of the brain is notoriously difficult to measure due to its sea horse shape and its size (typically only four centimeters long). The entorhinal cortex of the brain is even smaller than the hippocampus, and it too is hard to discern reliably. Further, measurements should be made non-invasively to prevent interference with the normal operation of the brain. Similar issues are encountered when changes in the size and/or shape of other organs within the body are determined across a period of time.

As recognized by the present inventors, what is needed is a non-invasive means to measure the change in size of an object or portion of an object, such as an organ or segment of an organ (i.e., structure of the brain, chamber of a heart, and so forth). It is against this background that embodiment of the present invention were developed.

SUMMARY OF INVENTION

In accordance with one broad aspect of one embodiment of the present invention, disclosed herein is a method for measuring changes to an aspect of an object. The object is imaged during at least two different times, to produce at least a first (or "before") and second (or "after") image. The first and second images may be segmented, coregistered, and regions of interest defined in each image to observe, measure, and calculate changes to the desired structure of the object. Further, the region of interest may also be segmented to provide a more accurate analysis of changes, such as those specific to a given disease process.

In one embodiment of the invention, the object is a brain, and images are taken by magnetic resonance imaging. The embodiment may measure atrophy in a brain region occupied by the hippocampus and entorhinal cortex. Other embodiments may measure either atrophy or growth in other biological organs. Measuring growth by means of the present invention may be beneficial, for example, where non-invasive tracking of tumor size is desired.

Moreover, embodiments of the invention may focus on analyzing smaller regions of the brain while overcoming a known limitation of MRI scans—the presence of so-called non-uniformities in radio frequency signals when large areas are scanned—may be reduced.

In one embodiment of the invention, MRI scans and a computational formula are used to measure a region of the brain called the medial-temporal lobe over a time period of six months to several years. Loss of brain volume in medial-temporal lobe are converted to annual percent loss and compared with normative brain loss due to aging. Abnormally high rate of brain loss can be interpreted as a neurodegenerative process and used for diagnosis of dementia. The medial-temporal area contains the hippocampus and the entorhinal cortex, structures allied with learning and memory. The region holds about 30 cubic centimeters of brain matter in each hemisphere of the brain.

The present inventors found that each year this region of the brain shrank in people who developed memory problems up to six years after their first MRI scan. The present inventors conducted a study that followed a group of 45 healthy men and women over the age of 60 for six years. At the beginning of the study, everyone was within the normal range on a battery of tests typically used to detect early loss of memory and other mental skills. Each person received a MRI scan at the beginning of the study and (at the minimum) another one two years later. Thirteen people in the study declined, the rate of atrophy in the medial-temporal lobe was the most important variable observed by the present inventors that distinguished them from the normal aging individuals. The region lost about 0.7 percent of its volume annually (smaller than the size of a pea), while in the normal aging subjects, the region shrank by less than half that volume. In this study, an embodiment of the present invention was about 90 percent accurate, meaning that it correctly predicted cognitive impairment in nine out of 10 people over the six-year course of the study.

Other features, utilities and advantages of the various embodiments of the invention will be apparent from the following more particular description of embodiments of the invention as illustrated in the accompanying drawings.

DESCRIPTION OF PREFERRED EMBODIMENTS

1. Overview

Figure 1:
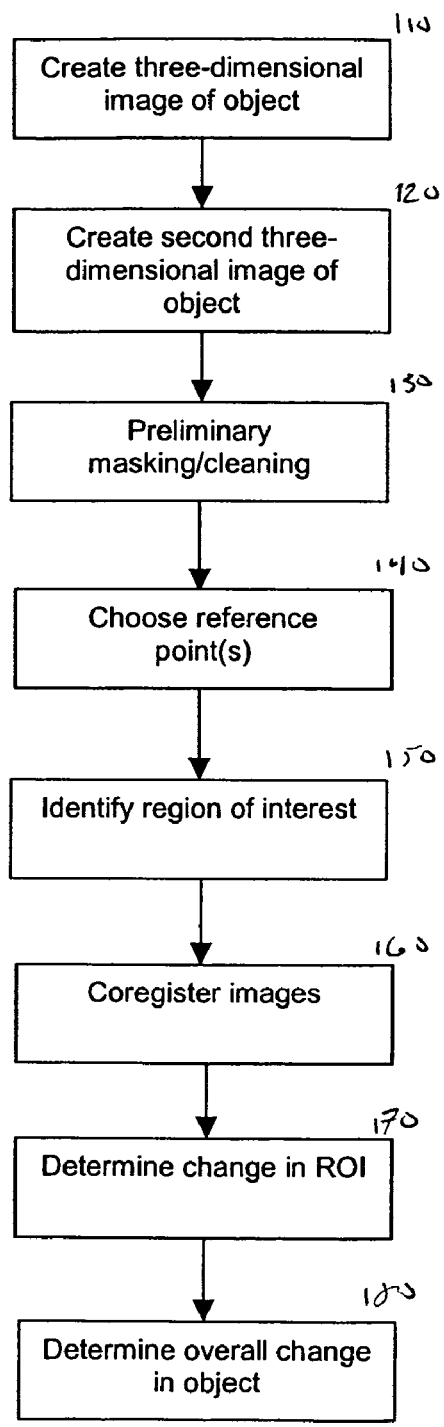
FIG. 1 is a flowchart depicting the general operations of an embodiment of the present invention.

One embodiment of the present invention takes the form of a method and apparatus for determining a change to a geometric structure. The change may be determined through an exemplary sequence of steps. FIG. 1 depicts a flowchart setting forth these general operations. Although the operations performed by the present embodiment are given in a specific order, it should be understood that some or all of these operations may be performed in orders differing from that set forth herein without impacting the spirit or scope of the invention.

Typically, the various operations described herein may be executed by computer-readable software operating on a properly-configured computer. The exact nature of the software and computer hardware may vary in different embodiments. Accordingly, it is contemplated that any computing device capable of running appropriate software may implement the operations described herein.

First, the object may be three-dimensionally imaged in operation 110. As a specific example of imaging, a magnetic resonance image (MRI) of the object may be taken, although other methods of imaging may also operate in the context of the embodiment. For example, the object may be scanned or a series of digital pictures taken in the event that changes in the object visible from the object exterior are to be determined. MRIs prove useful where changes to an interior element of the object are to be determined, and especially where the interior element is not visible from the object's exterior. A computed axial tomography (CAT) scan, positron emission tomography (PET) and single photon emission tomography (SPECT) may also facilitate such imaging.

After a time interval, a second image of the object may be created in the manner discussed above, in operation 120e.

The image of the object may then be subjected to a preliminary graphical segmentation and, if necessary, cleaning in operation 130. The digital image is divided into a number of voxels. A voxel, as is known in the art, is the smallest distinguishable box-shaped segment of a three-dimensional image. A mask of the object may be constructed within the image as part of the graphical segmentation. The mask typically contains only those voxels representing the object itself; voxels representing portions of the image outside the object are excluded from the mask. A discussion of matching voxels with either the object or non-object portion of the image is set forth below in the sections entitled "Segmenting the Region of Interest" and "Computing a Volume of the Region of Interest."

Typically, in operation 140 at least one common reference point within the mask is also chosen on both the before and after image. The reference point may be a visually distinct portion of the image, or may be a set of coordinates relative to the boundaries of the mask. For example, the centroid ("center of gravity") of the mask may be determined and used as the common reference point. Alternatively, a distinct anatomical features of the image may be identified as the reference point. The reference point (or points) ideally is present in each image and mask of the object, and serves to prealign masks of the object created at different times, as discussed below.

Next, in operation 150 a region of interest (ROI) is mapped. In broad terms, the region of interest is the portion of the object in which the change is to be determined. The voxels representing the region of interest may be marked, tagged, stored, or otherwise identified. The ROI may be mapped by a user, who may select the ROI by means of an input device such as a mouse. Alternatively, the ROI may be automatically mapped by the embodiment, which may determine the ROI based on certain criteria of the image. Typically, ROIs are constructed only with respect to the first ("before") image. The embodiment superimposes the second ("after") image on the first image, and thus may employ the first image's ROI with respect to the second image. Alternative embodiments may determine the ROI only with respect to the second image, effectively reversing the superimposition just discussed. Yet other embodiments may determine the ROI for both images.

The two images may then be compared to one another in operation 160. As part of this comparison, the invention coregisters images. Coregistration generally refers to the process of aligning the two images and ensuring that a given coordinate or voxel in the first image aligns with the same coordinate or voxel in the second image. Coregistration may include, for example, the exclusion of certain voxels from the image, forming a set from remaining voxels, spatially transforming the set for each picture, and/or mathematically matching voxel size between images (either anisotropically or by conversion to cubic voxels). Images may be resampled once coregistered. It should be noted that the coregistration process, as with all steps and processes of the present embodiment, may be automated.

Once the two images are coregistered (and the ROI in each optionally segmented), the change in the ROI between images may be determined in operation 170. The ROI may be compartmentalized, such that different compartments contain voxels corresponding to different materials within the object. For example, where the object is a human or animal brain, a first compartment may represent healthy tissue, while a second compartment may represent cerebrospinal fluid (CSF).

With respect to such an embodiment, neuronal degeneration is thought to manifest as degradation of healthy tissue, which is believed to be replaced by CSF. In another exemplary application, a tumor may be assigned to the first compartment, and healthy surrounding tissue assigned to the second compartment. Thus, the present embodiment may be employed not only to determine changes in brain tissue, but also the growth or shrinkage of any human or animal organ.

Typically, one compartment within the ROI will correspond to the element in which a change will be measured. The signal intensity for all compartments may be determined for both the first and second images and used in operation 180 to compute the volume of each compartment, for each image.

In the manner discussed above, the present embodiment facilitates high-precision measurement of changes in tissue and/or organs.

In the preferred embodiment, the measurements take place in each region of interest independently of other ROIs, rather than across the entire object.

This may, for example, minimize the variation in contrast, signal intensity, or other parameters between the segmented portions of the first and second images, when compared to such variations between the entireties of the first and second images. Essentially, because the region of interest is smaller than the entire image in each case, the variations in parameters between regions of interest are typically smaller than the variances in the same parameters between entire images. This, in turn, may permit normalization (as discussed below) of the regions of interest to a finer degree than is possible if all of the first and second images are normalized. A "finer degree" of normalization generally refers to a normalization having a lower error rate caused by mis-classifying voxels and such that results in more reproducible and reliable measures of atrophy.

2. Object Imaging

Generally, an object may be imaged in any manner that provides a three-dimensional image of an object. For example, an object may be imaged by means of magnetic resonance, computed tomography, position emission tomography, single proton emission computerized tomography, and so forth.

Many times, images of an object may contain images of elements adjacent or otherwise near the object of interest. For example, where the object is an organ, the object image may include nearby bone, blood vessels (and blood), fat, muscle, other organs, and so forth.

Object may be re-imaged at a later time, but its position and orientation within the scanner field of view will differ across time.

3. Image PreSegmentation

The segmentation of an image is generally discussed in U.S. Provisional Application Ser. No. 60/623,840, entitled "System, Software Arrangement and Method for Segmenting an Image," filed on Oct. 29, 2005, the entirety of which is incorporated herein by reference. Generally, "segmentation" refers to the process of selecting a particular portion, or segment, of a three-dimensional image. The segment is not restricted to any particular dimensions, and may have a height, width, and depth as desired.

Additional methods of image segmentation are well known to those skilled in the art, and may be used with the invention described herein without altering the spirit or scope of the invention. For example, where the object is a brain, the brain may be segmented by means of the brain extraction tool, brain surface extraction, or Minneapolis consensus strip techniques.

The image may be initially segmented to separate the object from surrounding elements. This segmentation operates at a gross level to more clearly define the object and distinguish it from irrelevant portions of the image. Segmentation may include, for example, assigning each voxel to one of two sets. The first set consists of all voxels representing a portion of the object, while the second set consists of all voxels not representing a portion of the object. This determination may be based on the signal intensity or contrast of each voxel, so that voxels having a signal intensity above a certain level are assigned to a first set while voxels with a signal intensity below the same level are assigned to a second set. (Whether the first or second set represents the object depends, in part, on the image.) In some embodiments of the invention, voxels having an intensity equal to the threshold level may be assigned to the first set, while in other embodiments such voxels are assigned to the second set.

Once all voxels are assigned, the mask of the object may be constructed simply by reference to the set containing the voxels corresponding to the object. Typically, both the first and second (or "before" and "after") images are segmented.

It should be noted this initial segmenting operation is entirely optional. Many embodiments of the present invention ignore this operation, and instead proceed to coregister the two images.

4. Coregistration

Figure 2:
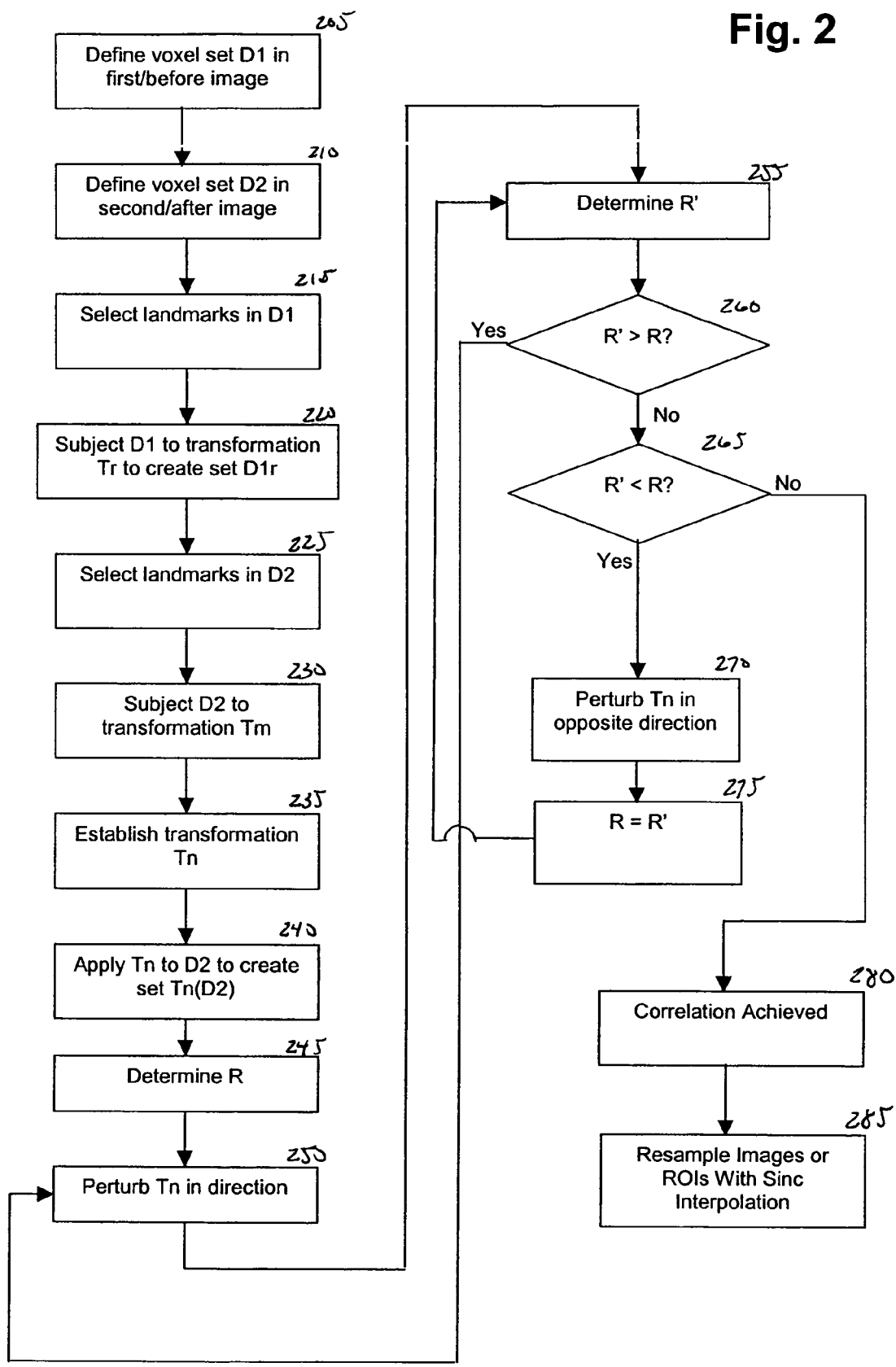
FIG. 2 is a flowchart depicting the operations executed by the embodiment of FIG. 1 when coregistering two images.

After the optional segmenting of both the before and after images, the images may be coreigstered. Coregistration is the process of aligning the images so that the object may be successfully mapped from one image to another. Coregistration may or may not involve scaling the images such that the object is the same size in each image, and/or occupies the same coordinates in each image. FIG. 2 is a flowchart depicting the general coregistration process.

In the present embodiment, coregistration is typically handled as follows. The before image includes a voxel set D1 representing the object, while the after image includes a voxel set D2 also representing the object. (It should be noted that D1 and D2 more accurately represent at least a portion of the object, and may not necessarily represent the entire object.) Voxel set D1 is determined in operation 205, and voxel set D2 is determined in operation 210.

A user may select a number of landmarks in set D1 in operation 215. For example, landmarks L1, L2, and L3 may be selected. Alternative embodiments may employ more or fewer landmarks. Each landmark is typically an easily-identifiable visual feature distinguishable in the image. For example, where the object is a brain, three landmarks may be selected: the right optic nerve anterior to the eye; the left optic nerve; and the superior culliculi. In some embodiments, a computer may automatically select the landmarks from the image. Such automatic selection may occur where multiple variants on, or examples of, a basic object are imaged and each such variant includes similar features. To continue the example above, the landmark selection process may be automated to choose the optic nerves and superior culliculi because these biological structures have a similar appearance in each image of a brain taken with the same imaging technology.

Next, a rigid body transformation Tr is computed in operation 220. The rigid body transformation maps set D1 to a standardized anatomical reference system D1r. The system D1r is a coronal view in which both eyes are on the same level and in which the interhemispheric plane is aligned with the yz plane. Transformation Tr is a "rigid body" transformation because the transformation neither stretches nor shears the before image. Rather, the transformation Tr axially shifts and/or rotates the image to match the system Dlr. The transformation Tr yields transformed landmarks Lr1, Lr2, Lr3.

After this transformation, the user (or automated system) may select the same landmarks from the set D2 of the after image. This is operation 225. (It should be noted operation 225 may occur before operation 220.) For convenience, these landmarks will be referred to as M1, M2, and M3, corresponding to landmarks L1, L2, and L3, respectively. Each landmark selected from the set D2 corresponds to a landmark selected from the set D1; accordingly, the number of "M" landmarks matches the number of "L" landmarks.

A second rigid body transformation, transformation Tm, is computed to map each landmark M1, M2, M3 onto their corresponding transformed landmarks Lr1, Lr2, Lr3. This process occurs in operation 230.

A third rigid body transformation Tn is determined through successive iterations, as shown generally in operations 235-275. The transformation Tn refines landmark matching-based coregistration, and generally maps voxels from the set D2 to the set D1r. At the beginning of each iteration process, an arbitrary transformation Tn is generated in operation 235. The arbitrary transformation Tn is then applied to the voxels of the set D2, to yield the set Tn(D2), as operation 240. The embodiment then computes the measure of image similarity between voxels in the set D1r and voxels in the transformed set Tn(D2). The measure of image similarity is typically a correlation, denoted by R, of the signal intensities of corresponding voxels in each set, and is performed in operation 245.

In operation 250, the transformation Tn is perturbed by a small amount of rotation and/or translation. Typically, such perturbations are on the order of a single degree of rotation, and a single millimeter of translation. Alternative embodiments may vary these measurements.

Once perturbed, operation 255 is executed and the correlation R' between the voxels of the set Tn(D2) and D1r is measured. If the correlation improves so that R'>R (that is, if the signal intensities of corresponding voxels is closer than prior to the transformation Tn), the transformation Tn is perturbed in the same direction as before. This determination corresponds to operation 260. This direction of perturbation encompasses additional perturbations both in rotation and translation.

If, however, the correlation between sets decreases (i.e., R'<R), which is determined in operation 265, the transformation function Tn is perturbed in a direction opposite the last perturbation as shown in operation 270. Following such perturbation, operation 275 sets R equal to R', and returns to operation 255. This permits a new R' to be determined and the set correlation to be reexamined in operations 260 and 265.

Thus, for example, if the last perturbation moved the voxels of set D2 a millimeter left and one degree clockwise, and this results in an decrease in correlation, the next perturbation of Tn would move the voxels of set D2 a millimeter right and a degree counter-clockwise.

If the perturbation of function Tn yields no significant changes between R and R', then convergence has been achieved and the first and second images are coregistered. This is represented by operation 280. Accordingly, the third rigid body transformation is complete.

Finally, once the images have converged, each image is resampled using sinc interpolation in operation 285.

5. Defining the Region of Interest

As previously mentioned, the embodiment may define a region of interest within the overall image. The region of interest is typically smaller than the entire image. Defining a ROI may permit finer segmentation (and thus less error) than if no ROI were defined and segmentation applied solely to the entirety of each image.

In one embodiment, a user may define the ROI through the use of a mouse or other input device connected to the embodiment. The user may position the mouse pointed on the center of the ROI and click the mouse button. The embodiment may then generate a box centered on the chosen point. The dimensions of this box may vary, and may be specified by the user or the embodiment.

For example, where the ROI is the hippocampus of the brain, the embodiment may generate a box centered on the chosen point within the hippocampus, with horizontal and vertical dimensions equal to 25% extents of the cranial cavity. This box may be propagated in the z direction (like a cookie cutter across coronal images) to encompass a slab extending between the anterior and the posterior margin of the hippocampus.

Alternative embodiments may automate the selection of the ROI. For example, there are several software products that generate standard brain ROIs using a technique of template matching known to those skilled in the art. In this promising technique, individual scans are transformed or "morphed" using a geometric transformation $T_{morph}$ to a standard anatomical template. Standard ROI are prepared on the template. The inverse transformation $T^{-1}_{morph}$ is then applied to each template ROI, yielding ROI's in the original subject's space.

6. Segmenting the Region of Interest

Figure 3:
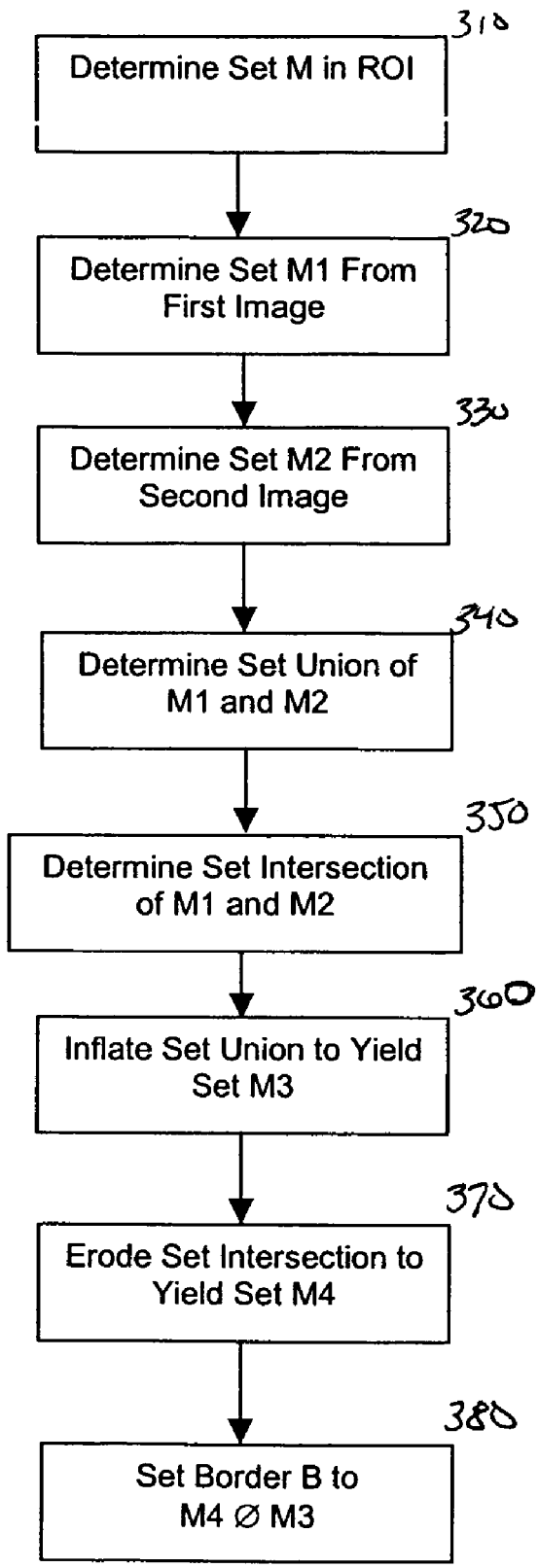
FIG. 3 is a flowchart depicting the operations executed by the embodiment of FIG. 1 when segmenting a region of interest.

The ROI may be segmented in a manner similar to that previously discussed with respect to the portion of the image corresponding to the entire object. Segmenting across the smaller region of the ROI, however, typically minimizes the difference in contrast and/or signal intensity between the before and after images, and thus may minimize overall error resulting from segmentation. FIG. 3 generally depicts the operations in this segmenting process for the ROI.

Initially, in operation 310 the embodiment determines a set M though the procedure disclosed in U.S. provisional application Ser. No. 60/623,840, or an equivalent method. Such segmentation has been previously discussed.

From the set M, an object border may be determined by the present embodiment. First, in operation 320 the stripped object set M1 is determined from the first image. Next, in operation 330 the stripped object set M2 is determined from the second, coregistered image. Because the images are coregistered, they are approximately equal in size and alignment.

In operation 340, the embodiment may then determine the set union between sets M1 and M2, expressed as M1∪M2. In operation 350, the embodiment may further compute the set intersection between these sets, expressed as M1∩M2. Each set, along with the union and intersection between the sets, contains a number of voxels.

After the set union and intersection are determined, operation 360 is executed and the union may be inflated by a set amount to yield a third set. The union is "inflated" by subjecting the set to a three-dimensional growing operator. That is, each voxel within the union is expanded by the operator In a specific embodiment configured to determine a change in size in the hippocampus of a human brain, the union may be inflated by two millimeters. The inflated union is expressed as set M3. Inflation generally changes the boundaries of the set, and potentially the number of voxels in the set M3.

In operation 370, the embodiment may also shrink the intersection between sets M1 and M2 by subjecting the voxels in the intersection to a three-dimensional erosion operator. The erosion operator deletes from the set intersection all voxels that lie on the intersection's surface. In the specific embodiment configured to determine a change in the size of the hippocampus of the human brain, the intersection may be shrunk by two millimeters. The eroded intersection is expressed as set M4. It is referred to below as the interior part of the object within a given ROI.

Finally, in operation 380 the border region B is set to equal M4⊘M3, where ⊘ is the set difference operator. This defines the border of the ROI, and thus completes the ROI segmentation.

7. Normalizing an ROI and Computing a Volume of the ROI

After the border of the ROI is adequately defined and the ROI segmented, the volume of the ROI may be computed. Since the ROI is typically the portion of the object for which a measurement is desired, computing the change in volume between the first image and second image yields the desired change in the object's structure.

Figure 4:
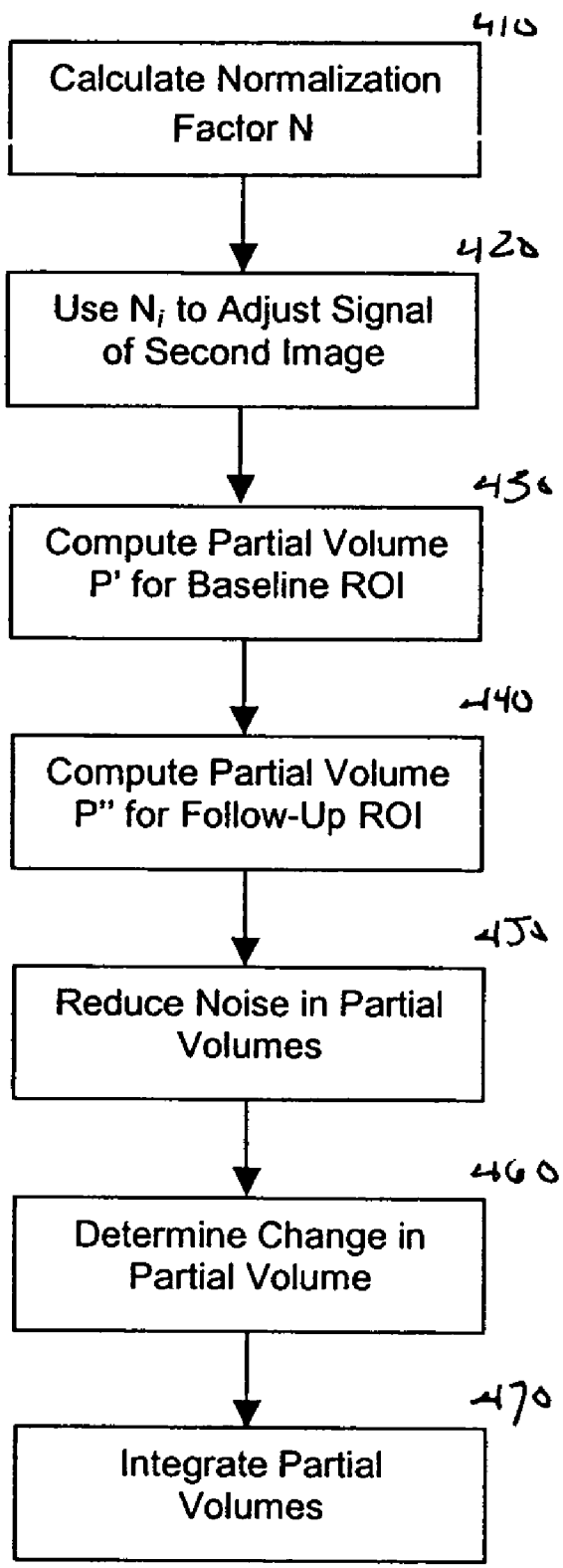
FIG. 4 is a flowchart depicting the operations executed by the embodiment of FIG. 1 when computing a partial volume for the region of interest.

Referring now to FIG. 4, the embodiment initially computes a normalization factor $N_i$ for the ROI in operation 410. This factor is typically based solely on the interior region of the ROI (see set M4 above). To calculate the normalization factor, the embodiment employs $S'(Int_i)$, defined as the average signal intensity of the interior part of the ROI at the baseline (i.e., in the first image), and $S''(Int_i)$, representing the average signal intensity of the interior part of the region at follow-up (i.e., in the second image).

In operation 420, the embodiment sets $N_i = S'(Int_i)/S''(Int_i)$. The normalization factor is used by the embodiment to adjust the signal of the second image, as follows.

The embodiment may scale the follow-up signal intensity of each voxel within the ROI by the factor $N_i$. That is, $R'' = N_i * S''(Int_i)$. This adjusts the signal intensity of the second image to be in-line with the signal intensity of the first image. Alternative embodiments may normalize the ROI of the first image by adjust the first image's signal, or may normalize the ROI of both images by adjust both images' signals to match a third value (such as a predetermined constant).

In operation 430, the embodiment may now compute a partial volume P' for of each voxel v from the border component of the baseline ROI, as follows:

$$P'(v)=1-[S'(Int_i)-S'(v)]/[S'(Int_i)-c'S'(Int_i)]$$

Generally speaking, this expression employed by the embodiment is a linear function of $S'(v)$. Thus, the embodiments sets $P'(v)$ to one for voxels of intensity matching the interior region, and set $P'(v)$ to zero for voxels with signal intensity matching a background signal of $c'S'(Int_i)$. The constant c' for a given first and second image represents the contrast between the object and the background. As one example, the object may be a brain and the background cerebral spinal fluid.

Next, in operation 440, the embodiment may compute a partial volume P'' for of each voxel v from the border component of the follow-up ROI, as follows:

$$P''(v)=1-[R''(Int_i)-R''(v)]/[R''(Int_i)-c''R''(Int_i)]$$

The embodiment employs a constant c'', which is determined for the second (follow-up) image. The constant c'' accounts for possible changes in the contrast between the object and the background in the second image. It should be noted c' and c'' may be equal, but need not necessarily be so. Further, c' and c'' may vary with each set of images, insofar as they are dependent on the contrast variances in their respective images. The constants c' and c'' represent the ratio between the signal intensity (also referred to as "brightness" or "luminosity") of the background versus the signal intensity of the object of interest in their respective images.

Additionally and optionally, the present embodiment may act to reduce the noise present in the partial volumes in operation 450. To reduce noise, the embodiment may postprocess or filter each partial volume P as follows. First, the variable epsilon is set to equal the estimated noise level of the partial volume. Next, the embodiment determines if P is less than epsilon. If so, then P is set to zero. If P is not less than epsilon, the embodiment determines whether P is greater than (1−epsilon). If so, P is set to one. If neither condition is met, the value of P remains unchanged.

With this data, the embodiment may determine the partial volume change for of each voxel v from the border component of the ROI. This is represented on FIG. 4 as operation 460 The embodiment calculates the partial volume change $\Delta P(v)$ as follows:

$$\Delta P(v)=P'(v)-P''(v)$$

Finally, in operation 470 the embodiment integrates or simply adds up the partial volume change for each voxel v over the border component of the ROI. This yields the overall volume of the ROI.

8. First Clinical Study

A discussion of a first clinical study used to evaluate the operation of the present embodiment follows. Generally, and as set forth in more detail in the discussion of the study, below, the present embodiment was used to measure the atrophy of the hippocampus region of the brain. That is, brain was imaged by magnetic resonance imaging, and the change in size of the hippocampus was measured. Accordingly, the hippocampus is the ROI for the first study.

Subjects of the first study were volunteers. Fifty-five elderly individuals have relatively normal cognitive faculties for their age participated in the first study. All were high school graduates and 76% (42/55) had education beyond high school. Subjects were given an extensive screening and diagnostic battery to establish a baseline, including medical, neurological, psychiatric, family history, and a comprehensive battery of neuropsychometric tests. At least three observations were acquired on all subjects, with 47% subjects having four or more observations. These observations were on the average 2.2 years apart.

The measures used to assess cognition and memory included certain tests well known to those skilled in the art, including: the Global Deterioration Scale (GDS); the Mini-Mental State Examination (MMSE); and the Guild memory test. In many cases, additional tests designed to measure recall, visual recognition memory, and spatial recall were also employed.

Baseline selection criteria for test subject included a GDS score≦2, a MMSE score≧28, age≧60, no contraindications to MRI scanning, absence of gross brain abnormalities, and no evidence of neurological, medical, or psychiatric conditions that could affect cognition. At the time at which the baseline was established, all subjects were free of clinically detected cognitive impairment in memory, concentration, orientation, language, executive function or activities of daily life.

Individuals were prospectively followed over six years to ascertain who remains cognitively normal and who declined. MCI status was defined as: (a) GDS=3, indicating a decline in functioning (including memory complaints) corroborated by an informant and determined by the examining physician, (b) selective memory impairments as demonstrated by neuropsychological memory test score that is 1.5 standard deviation below that of normal elderly of matching age, gender and education; and (c) subject not meeting criteria for dementia. The statistical distribution of the memory test scores required in point (b) was derived from a database of 282 observations on normal subjects aged 60-87. The diagnosis of Alzheimer's disease was made according to generally accepted National Institute of Neurological Disorders and Stroke—Alzheimer's Disease and Related Disorders Association (NINDS—ADRDA) criteria.

Serial magnetic resonance imaging was used to construct all images for all subjects. Among the 55 high-functioning normal elderly individuals recruited, 45 successfully completed the second scan within 40 months after the first scan and formed the study cohort. The majority of subjects 78% (35/45) had a second MRI study within 20-28 months of the baseline study, 7% (3/45) were reexamined with MRI at 6-19 months, and 16% (7/45) at 29-40 months. Three-dimensional T1-weighted MRI were performed on a 1.5 tesla scanner (manufactured by GE Signa, General Electric, Milwaukee) using a spoiled gradient-recalled acquisition in the steady state sequence, with the following acquisition parameters: TR 35 ms, TE 9 ms, NEX=1, 60° flip angle, 256×192 acquisition matrix, 1.2 mm section thickness, 18 cm FOV, and 124 contiguous coronal slices.

Analysis was performed blinded to all clinical data, including coregistration of the baseline (i.e., first or before) image and later (i.e., second or after) images. Coregistration between images was achieved by determining an inter-hemispheric plane based on landmarks and defined as the yz plane. Voxels outside the brain were automatically isolated from the brain mask. The mask was constructed as the largest contiguous structure that is only weakly connected to adjacent structures (e.g., optic nerve connection to the eyes). A cost function C reflecting the similarity of the baseline and the follow-up images within the brain mask was then evaluated. The cost function, and operation thereof, is known to those skilled in the art. A rigid-body spatial transformation minimizing C was used to produce registered images. Further, tri-linear interpolation was used to compute C during minimization. Anisotropic voxel size was taken into account mathematically, without interpolation to cubic voxels. Upon convergence, the images were resampled using sinc interpolation and the maximum left-right and cranio-caudal extents of the brain were recorded. Biases are avoided by resampling both baseline and follow-up images exactly once. Generally, this coregistration process took approximately a half hour for each set of images.

Next, the medial-temporal lobe (MTL) region was defined. A box-shaped bilateral MTL region of interest was generated using simple criteria. Horizontal and vertical box sizes were defined as 0.25 times the left-right and cranio-caudal dimensions of the brain. The anterior plane was defined by the appearance of the pes hippocampus, and the posterior plane by the anterior crux of the fornix.

To further define the ROI, a user of the embodiment used to perform the study was presented with a coronal image located midway between these two planes. The user then selected the centers of the left and the right hippocampus with a mouse click, and these centers become the centers of the left and the right MTL boxes (and thus the center of the MTL ROIs). A "whole brain" ROI was generated automatically by extending the brain parenchyma three layers of voxels. The MTL ROIs were generated by one individual and for each case its location was verified by at least two individuals.

To test the sensitivity of positioning of the box on the atrophy measures, each coordinate that defines the MTL box was subject to a random +/−4 mm perturbation. For each of the 45 study subjects, the original and the perturbed regions were analyzed and the two results were tested for agreement.

Once the ROIs were defined, atrophy of the hippocampus could be computed. Volumetric analyses of serial MRIs were performed by decomposing the brain volume into its interior E and border B components. First, a set M was constructed by selecting voxels at the gray level above 0.55 W, where W is the signal of the white matter. The constant 0.55 was determined empirically using phantom studies. The volume ($V_E$) and the mean MR signal intensity ($S_E$) of the interior region E were next computed. Brain border B was constructed as a 3D shell that initially spans the baseline and the follow-up edges of the set M. B was then extended two voxel layers inwards and two layers outwards. Extending the border in this fashion renders the process less sensitive to errors resulting from coregistration, and further facilitates a more meaningful assessment of the partial volume effect that may result in blurred edges for the boundary. On this note, it should be understood that any embodiment may extend the border B in this manner for any object image or region of interest.

For each voxel in B, the embodiment determined the partial tissue decomposition using a two-compartmental model. In the two-compartmental model, the embodiment initially presumed that only the brain and CSF (cerebral spinal fluid) contribute to the signal s. In such a case, the following equations are true:

$$b+c\ v$$

$$S_E * b + S_c * c = s,$$

where v is the voxel volume, and b, c are the partial volumes of the brain and CSF within the voxel. Similarly, $S_E$ is the signal intensity of the interior E, while $S_c$ is the signal intensity of cerebral spinal fluid. The embodiment solved the above equations for b and c; these values were then integrated over the entire 3D ROI. It should be noted that values $S_E$, $S_c$, may vary across brain regions due to MR signal nonuniformities. The signal intensity of CSF, denoted above as $S_c$, is computed from $$S_c = r S_E,$$

where r is the contrast between CSF and the brain, assumed to be constant across brain regions.

The value r=0.32 for the T1-weighted imaging sequence was empirically determined from phantoms and reference T1's of mature brain tissue at 1.5 tesla (34). Average T1 of the cerebral gray and white matter was used (T1=820 ms). Since the scanner and the imaging sequence did not undergo changes within the study period, r was treated as a constant by the embodiment.

It should be noted that the empirically-derived values and constants discussed with respect to this trial may vary between objects subjected to the operation of the present embodiment. Accordingly, such values and constants are exemplary in nature.

The embodiment defined the atrophy for each ROI and each scan as the ratio of the CSF volume to the total ROI volume. The annual atrophy rate in each ROI was expressed as baseline volume minus the follow-up brain ROI volume, divided by the baseline volume, and by the time between the two MRIs.

The embodiment then performed statistical analysis on the images, concentrating on the ROIs. Logistic regression was used to construct a model relating the clinical outcome (decline/no decline) and independent variables: age at baseline, years of education, gender, whole brain and MTL atrophy at baseline, and whole brain and MTL atrophy rate (percent per year). Because of prior observations, separate interaction terms between age and gender and atrophy rates were included. Forward stepwise selection mode (SPSS for Windows, version 10.0) was used, with iterative entry of variables based on test-score p<0.05, and removal of variables based on probability 0.10 of likelihood-ratio statistics. For each variable in the equation the embodiment examined its coefficient, standard error of the coefficient, estimated odds ratio and its confidence interval. Minitab software (Minitab version 13) was used to compute exact confidence intervals for proportions.

Tables 1 and 2 provide the demographic description and the distribution of measured neuroimaging variables at the baseline, the end of year 2, and at the completion of the study. After an average of 6.1 years of observations, 32 subjects remained normal and 13 declined to a diagnosis of MCI (n=9) or to mild to severe Alzheimer's disease (n=4). Of the 13 that declined, seven declined before and six declined after the first follow up interval. Examination of the medical records and MRIs indicated that none of the declining subjects experienced any neurological, medical, or psychological event that could account for the observed decline.

TABLE 1

Study subjects and grouping by clinical outcome

| | All (N = 45) | NL->NL (N = 32) | NL->DECL (N = 13) | p* |
|---|---|---|---|---|
| Gender (male/fem/% fem) | 20/25/56% | 12/20/63% | 8/5/38% | 0.19 |
| Education (yrs) | 15.5 ± 2.3 | 15.7 ± 2.5 | 14.9 ± 1.9 | 0.32 |
| Age at baseline (yrs) | 69.8 ± 5.4 | 68.2 ± 5.1 | 73.6 ± 4.1 | 0.002 |
| APOE type (E4+/E4-/% E4+) | 10/34/22%# | 7/25/22% | 3/9/23%# | 0.33 |
| GDS, baseline | 1.91 ± 0.36 | 1.88 ± 0.42 | 2.00 ± 0.00 | 0.10 |
| GDS, year 2 | 2.40 ± 0.47 | 2.09 ± 0.47 | 3.15 ± 0.90 | 0.001 |
| MMSE, baseline | 29.1 ± 1.0 | 29.2 ± 1.1 | 29.0 ± 0.8 | 0.59 |
| MMSE, year 2 | 28.5 ± 1.9 | 29.0 ± 1.2 | 27.1 ± 2.5 | 0.02 |

*Differences between the declining and nondeclining groups were compared using Fisher's exact test for gender and APOE genotype, and using t-test for all other variables.
APOE genotype not available for one subject. APOE stands for "apolipoprotein E gene."
NL = normal controls;
DECL = subjects with cognitive decline;
MMSE = Mini-Mental State Examination;
GDS = Global Deterioration Scale.

TABLE 2

Distribution of measured neuroimaging variables

| | All (N = 45) | NL->NL (N = 32) | NL->DECL (N = 13) | P value* |
|---|---|---|---|---|
| Brain CSF %, baseline | 20.9 ± 1.7 | 20.4 ± 1.6 | 22.1 ± 1.4 | 0.001 |
| Brain CSF %, year 2 | 22.1 ± 2.1 | 21.4 ± 1.8 | 23.9 ± 1.6 | <0.001 |
| MTL CSF %, baseline | 19.0 ± 3.7 | 18.0 ± 3.5 | 21.5 ± 3.2 | 0.004 |
| MTL CSF %, year 2 | 19.8 ± 4.1 | 18.4 ± 3.7 | 23.1 ± 3.3 | <0.001 |
| Brain atr. rate (%/y) | 0.78 ± 0.95 | 0.58 ± 0.42 | 1.28 ± 1.58 | 0.14 |
| MTL atr. rate (%/y) | 0.44 ± 0.45 | 0.26 ± 0.36 | 0.90 ± 0.30 | <0.001 |
| Male | 0.44 ± 0.40 | 0.20 ± 0.27 | 0.81 ± 0.26 | <0.001 |
| Female | 0.44 ± 0.50 | 0.29 ± 0.41 | 1.05 ± 0.31 | 0.002 |
| Age ≤ 70 y | 0.23 ± 0.37 | 0.20 ± 0.36 | 0.61 ± 0.18 | 0.007 |
| Age > 70 y | 0.63 ± 0.44 | 0.36 ± 0.36 | 1.03 ± 0.24 | <0.001 |

*P values for differences between the declining and nondeclining subject groups were calculated with the t test.
NL = normal controls;
DECL = subjects with cognitive decline.

Figure 5:
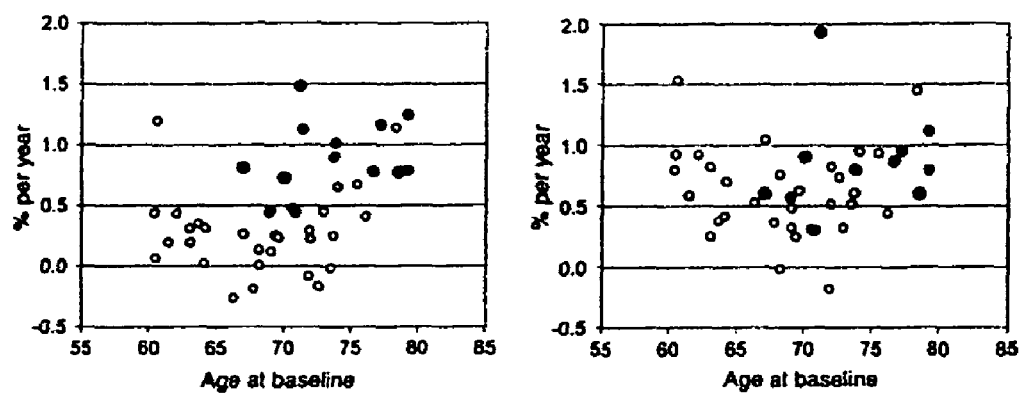
FIG. 5 illustrates graphical plots of annual atrophy rates in all subjects of study 1 versus their age at baseline, in accordance with a first clinical study.
Figure 10:
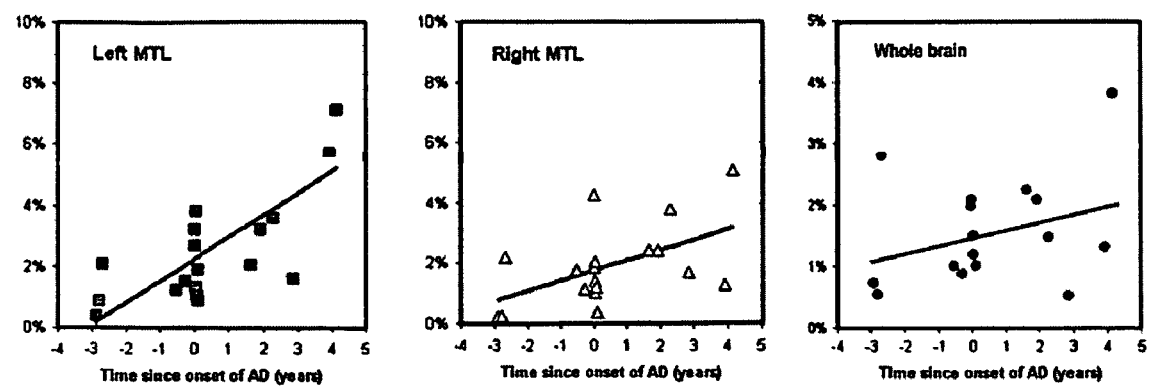
FIG. 10 is a graphical plot of annual atrophy rates in left and right MTL and the whole brain plotted against time since onset of Alzheimer's disease for patients in the second study.

FIG. 5 plots annual atrophy rates in all subjects versus their age at baseline. FIG. 10 illustrates three individual cases.

When testing the stepwise logistic regression model for main effects, MTL atrophy rate was found to be the only significant predictor of future cognitive decline. The overall accuracy of prediction was 89% (correct prediction in 40/45, 95% CI: 76-96%), with 91% specificity (29/32, 95% C.I. 75-98%) and 85% sensitivity (11/13, 95% C.I. 55-98%). The annual MTL atrophy rate of 0.7% best separated declining from nondeclining subjects. Overall, the odds ratio (OR) for cognitive decline was 1.7 (95% confidence interval 1.2-2.3) for each 0.1%/year of MTL atrophy rate as a risk factor. With interaction terms included in the model, the interaction between MTL atrophy rate and age, and the interaction between MTL atrophy rate and sex were the only two significant predictors of decline (see Table 2).

The regression model based on demographic and psychometric scores, including baseline and first follow up MMSE, achieved 76% (34/45, 95% C.I. 60-87%) accuracy. Adding MTL atrophy rate to this regression model significantly improved the classification (chi-square change p<0.001). Without the seven subjects who declined prior to the second MRI, the prediction model yielded essentially the same result: the MTL atrophy rate interactions with age and gender significantly predicted decline with an accuracy of 89% (34/38, 95% C.I. 75-97%). Positioning sensitivity analysis indicates that a random +/−4 mm error in position of the MTL box introduces a relatively minor error (one standard deviation=0.05%/year) in atrophy rate. The difference between the original and perturbed results did not correlate with atrophy rates (R=0.03, p=0.88).

9. Second Clinical Study

A second clinical study was also performed to test operation of the present embodiment and its accuracy in both measuring structural changes to portions of the brain and correlation between such changes and cognitive decline. In this further study the course of brain atrophy was evaluated in cases of sporadic Alzheimer's disease with a "known" date of onset. Subjects were selected for whom this date could be established with reasonable accuracy. Atrophy rate was assessed using serial MRI and a regional variant of a brain boundary shift integral. The results support the hypothesis that brain atrophy in the MTL region follows a fairly consistent course. In particular, the evidence showed that the relative MTL atrophy rate increases in the course of the disease.

Subjects were patients in the early stage of Alzheimer's disease, and were subjected to an extensive screening and diagnostic battery at baseline. Generally, images were taken of each patient's brain approximately every two years. Examinations consisted of medical, neurologic, and psychiatric evaluations, a comprehensive battery of neuropsychometric tests, and a comprehensive set of MRI acquisition sequences.

Figure 8:
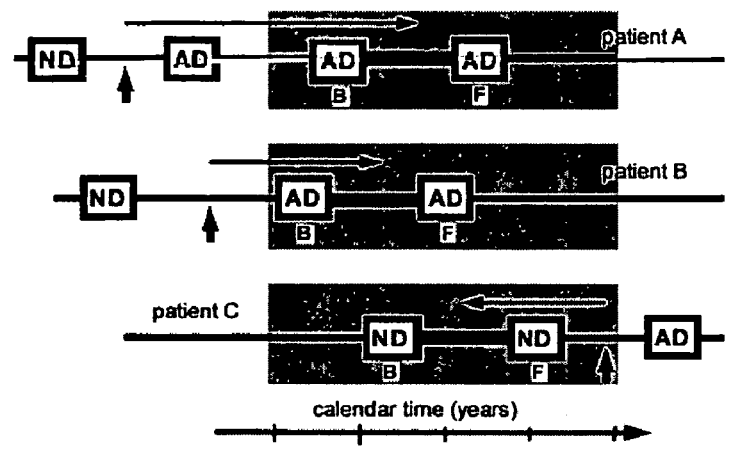
FIG. 8 is a schematic diagram depicting the design of a second study.

In order to assure the highest precision of measurement of brain change, the patients were required to undergo at least two MRI examinations in a time period or interval P during which neither the scan protocol nor the scanner were changed. FIG. 8 is a schematic diagram depicting the study design. Boxes labeled either ND or Alzheimer's disease represent the times at which a patient was imaged, examined clinically, and underwent psychometric tests. Alzheimer's disease indicates the diagnosis of probable Alzheimer's disease, ND indicates a mildly impaired status but no Alzheimer's disease, and the thick vertical arrows represent the estimated onset of Alzheimer's disease. The gray area shows the time period or interval P in which all baseline B and follow-up F scans occurred. Brain and cognitive changes taking place between the baseline and follow-up period (indicated by thicker intervals in the time-lines) were correlated in this study with the time since onset (TSO) of Alzheimer's disease (horizontal lines with thin arrows.) In patients A and B, both the baseline and the follow-up scans were performed after the diagnosis of Alzheimer's disease had been made. In patient C, TSO has a negative value, since the diagnosis of Alzheimer's disease was made after the MRI examinations.

Independently, each patient was required to have had two consecutive examinations, one with a negative diagnosis for probable Alzheimer's disease, and a follow-up in which the patient was first diagnosed with probable Alzheimer's disease. Thus, subjects selected satisfied the following four conditions: (a) on the initial examination the subject's cognitive impairment did not meet the Alzheimer's disease criteria recommended by National Institute of Neurological Disorders and Stroke—Alzheimer's Disease and Related Disorders Association (NINDS—ADRDA), (b) the subject was diagnosed with probable Alzheimer's disease according to NINDS—ADRDA on one of the follow-up examinations, (c) completed at least two high-resolution MR scans during a specific 4-year period P (see below), and (d) was free of MRI evidence of overt brain pathology such as tumor, stroke, hydrocephalus or significant trauma. Also excluded were individuals with a history of alcoholism, drug abuse, or psychiatric illness, and those with physical impairment that may adversely affect the neuropsychological testing.

Among the 78 Alzheimer's disease patients evaluated with serial MRI during the 4-year study period, 18 Alzheimer's disease subjects (5 men and 13 women) fulfilled the inclusion criteria (a)-(d). At the examination just prior to the examination when the Alzheimer's disease diagnosis was made, 15 out of 18 patients (83%) qualified for the commonly used guidelines for mild cognitive impairment that requires neuropsychological memory test score to be 1.5 SD below the mean score of normal elderly of matching age, gender and education. The statistical distribution of the memory test scores was derived from a database of 282 observations on normal subjects aged 60-87. Study subjects completed 13+/−2.5 years of education (mean+/−SD), had MMSE scores of 26.0+/−3.4 at baseline and 22.5+/−5.2 at follow up. The average MMSE extrapolated to the time of the onset of Alzheimer's disease (TSO=0) was 24.9. Subject's age at the time of the onset of Alzheimer's disease was 75.1+/−8.6. TSO ranged from −2.9 to 4.2 years.

To remove the bias related to variable time interval between visits, the date of Alzheimer's disease onset was defined as the "midpoint" between the date of the first visits at which Alzheimer's disease was diagnosed and the prior visit (thick arrows in FIG. 4). Because measurement of the atrophy rate involves two MRIs, the time since onset (TSO) of Alzheimer's disease was defined as the interval between the date of onset and the midpoint of the dates of these two scans. TSO was represented as a negative value when the baseline and follow up MRI occurred before the onset of Alzheimer's disease (see patient C in FIG. 4).

To investigate if the neuroimaging findings are particular to Alzheimer's disease patients and not a characteristic of normal aging, the atrophy measurements were applied to a control group of elderly (age>=60) subjects that were cognitively normal during the period P of their two MRI scans as well as in subsequent visits carried out to a minimum of four years after the end of period P. Control subjects also satisfied the above criteria (c) and (d). Normal cognition in controls was defined as maintaining a rating of less than or equal to 2 on the Global Deterioration Scale (GDS).

The measures used to assess cognition in the subjects included the Mini Mental State Examination (MMSE); paragraphs recall, paired associates recall, and the shopping list recall (immediate and delayed recall versions); designs test (immediate visual paired associates); the visual recognition span test; the digit symbol substitution test (an attention and psychomotor speed measure); and digits forward and backward (working memory) tests.

Three-dimensional T1-weighted MRIs were performed on a 1.5 tesla scanner (GE Signa, General Electric, Milwaukee) using a spoiled gradient-recalled acquisition in the steady state sequence. Each MRI used identical acquisition parameters: TR 35 ms, TE 9 ms, NEX=1, 60° flip angle, 256×192 acquisition matrix, 1.3 mm section thickness, 18 cm FOV, and 124 contiguous coronal slices.

The baseline scans were first resampled by the embodiment to align the yz plane with the inter-hemispheric plane and coregistered with the follow-up scan using an iterative method. The method is known to achieve sub-voxel accuracy. Both baseline and follow-up images were resampled exactly once using the sinc interpolation method.

Annual rate of brain tissue atrophy was derived both globally for the entire brain, including the cerebellum and the pons, and regionally for the left and right MTL. The pair of coregistered images was first segmented into interior I and "border" B brain regions. Brain border B was constructed as a 3D shell that initially spanned the baseline and the follow-up brain edges, then was extended two voxel layers inwards and two layers outwards. The interior region I consists of voxels that lie within the baseline and the follow-up brains, but not in B. Regions of interest (ROI) $R_i$ described below were intersected with sets I and B and individually assessed for brain and cerebrospinal fluid (CSF) content at baseline and at follow up. The mean signal of the region's interior $R_i \cap I$ (the symbol $\cap$ denoting an intersection of two sets) at baseline and at follow-up were computed and used as normalization factors in all subsequent computations. Such signal normalization helps to compensate for signal variability between the baseline and the follow-up scans. For each voxel in the intersection $R_i \cap B$, the partial volume of the brain and CSF were determined using a two-compartmental model. Brain volume within each region $R_i$ was then computed as the sum of $R_i \cap I$ and the partial volume of the brain in $R_i \cap B$.

Box-like MTL regions of interest (ROI) were defined separately on the left and the right hemisphere. The embodiment defined the MTL box to be proportional to the subject's premorbid brain size in order to eliminate the variability of the measurements due to differences in head sizes. The horizontal dimension was taken as one quarter of the maximum left-right dimension of the intracranial cavity. Similarly, the vertical dimension of the MTL box was equal to one quarter of the maximum cranio-caudal extent of the supratentorial space. Antero-posterior extent was guided by the appearance of the hippocampus. Specifically, the anterior boundary was defined by the posterior-most coronal slice sa showing the uncal sulcus. The posterior boundary P was defined by the posterior-most coronal slice sp containing the tail of the hippocampus and preceding the appearance of the anterior crux of the fornix. The operator selected the mid-hippocampal slice (sa+sp)/2 and identified the image coordinates of the centers lc rc of the left and right hippocampus. The MTL ROIs were then generated so that their centers were positioned on the points lc and rc. The "whole brain" ROI W was defined as the set union (sum) I∪B of the interior and the border regions.

For each of the three ROIs (right and left MTL box and the whole brain), the annual rate of atrophy A was expressed as the baseline minus the follow-up brain ROI volume, divided by the baseline volume and by the time interval between the two MRIs. The baseline atrophy was defined as the ratio of the CSF volume to the total ROI volume.

The embodiment performed a statistical analysis by using linear regression models were to evaluate the relationship between the MRI-measures and the TSO, as well as the relationship between the psychometric scores and the TSO. Logistic regression model was computed to classify normal and Alzheimer's disease subjects. SPSS (Windows ver. 11.0) was used for all statistical analyses. To account for the uncertainty in the date of Alzheimer's disease onset, taken as the "midpoint" between the date of last clinic visit $V_1$, prior to the diagnosis, and $V_2$, the first visit at which the diagnosis was made, the embodiment used the method of statistical resampling. For each case, the embodiment generated a vector V of independent random variables distributed according to a uniform probability density function in the time interval $[V_1, V_2]$. Repeated samples of vector V were used to compute the parameters and the significance of the regression model. Resampling process continued by doubling the number N of samples until the mean significance level $P_N$ of the regression differed from the corresponding values $P_{N/2}$ by less than 5 percentage points, i.e., $|P_N - P_{N/2}| < 0.05\ P_N$.

Figure 9:
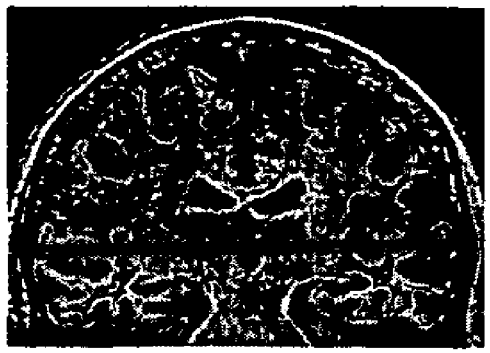
FIG. 9 are baseline and follow up images for three representative patients in the second study.
Figure 9:
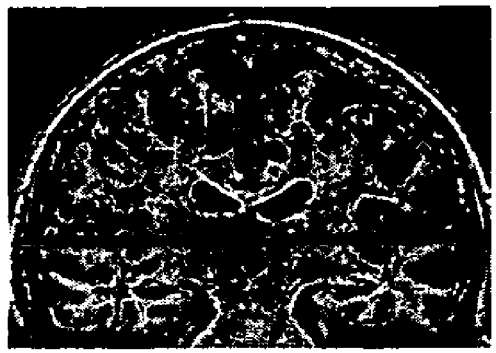
Figure 9:
Figure 9:
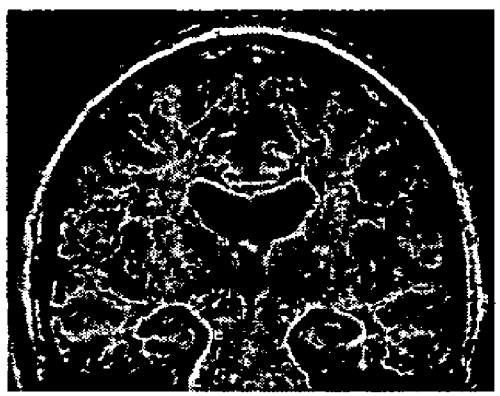
Figure 9:
Figure 9:

FIG. 9 illustrates the baseline and co-registered follow-up MRI images of three Alzheimer's disease patients. These images represent progressively advancing stages of Alzheimer's disease. The figure shows baseline images (left column) and co-registered follow-up coronal images (right column) for three representative patients. Top row: 65-year-old man imaged 2.9 years before the onset of Alzheimer's disease, annual MTL atrophy rate (A, %/year)=0.2 in the right MTL, 0.4 in the left MTL. Middle row: 76-year-old woman imaged at the time of onset, A=1.8 in the right MTL, 2.3 in the left MTL. Bottom row: 74-year-old woman, imaged 1.9 years after the onset, A=2.5 in the right and 3.2 in the left MTL.

A multivariate linear regression model was constructed to relate the annual atrophy rate A in the left MTL, right MTL, and in the entire brain as a function of the subject's age, gender, education level, and TSO.

TSO was a correlate of the atrophy rate for both the left MTL ($R^2=0.58$, p<0.001), right MTL ($R^2=0.30$, p=0.03) (see FIG. 6), and the left and right MTL combined ($R^2=0.48$, p=0.001).

Figure 6:
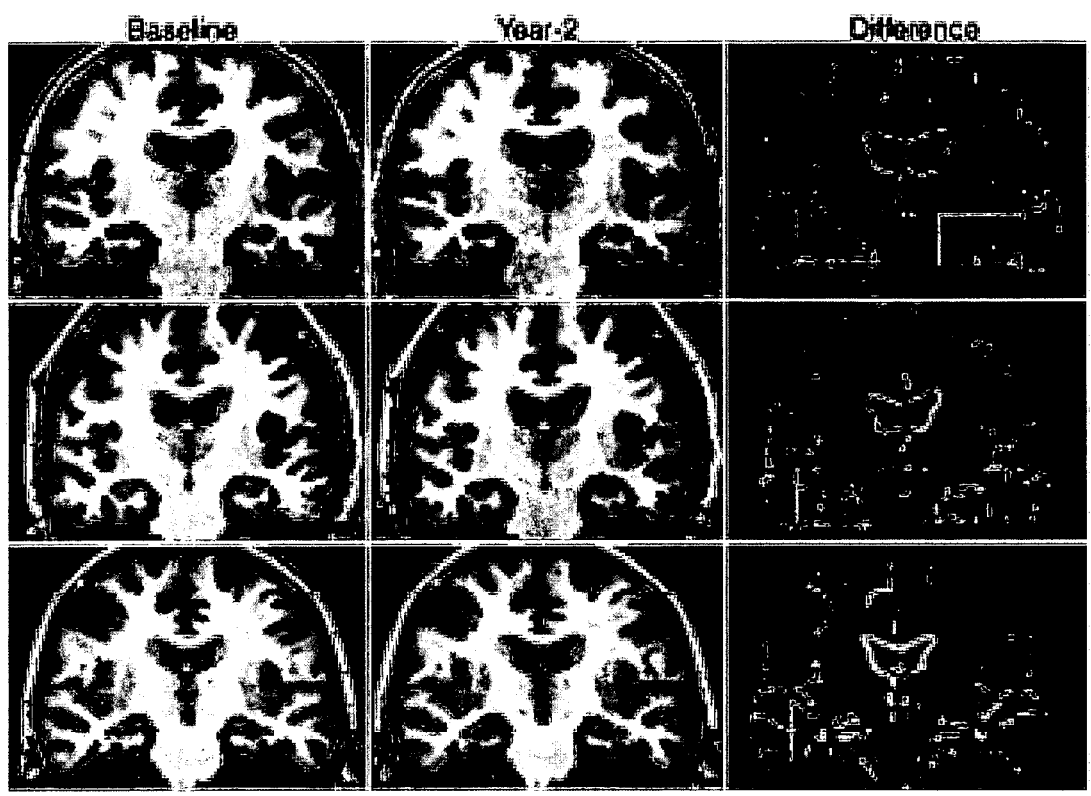
FIG. 6 illustrates images arising from three individual patients in study 1, in accordance with the first clinical study.
Figure 7:
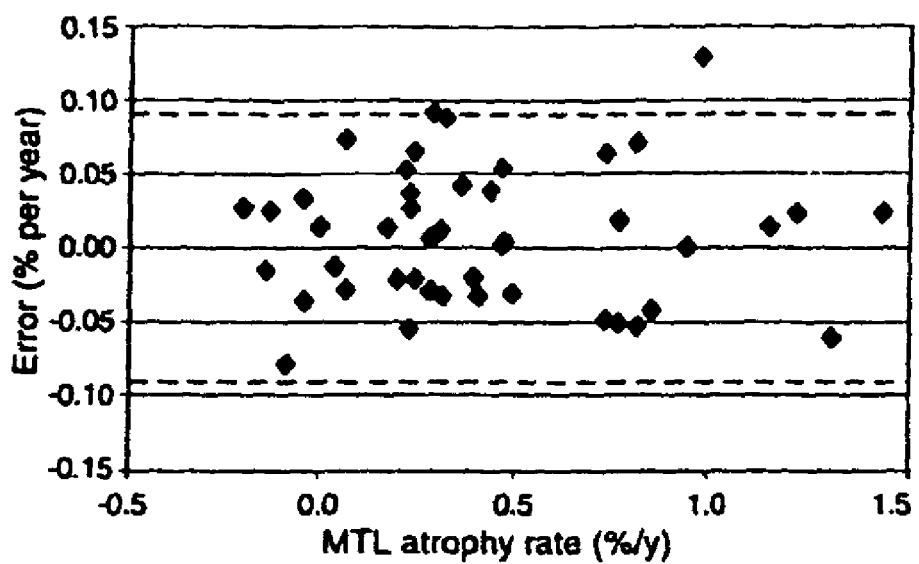
FIG. 7 is a graph deriving from study 1, which shows sensitivity of atrophy rate to the position of the MTL region, in accordance with the first clinical study.

In FIG. 6 annual atrophy rates (%/year) in the left MTL, right MTL, and the whole brain are plotted against the time since onset (TSO) of Alzheimer's disease. Both left and right MTL atrophy rates are significant correlates of TSO, with mean atrophy rates of 2.2 (left) and 1.8 (right) at onset. The annual increase of the left MTL atrophy rate is 0.73 (95% CI 0.36-1.08); it is 0.34 (95% CI 0.05-0.63) for the right MTL atrophy rate. No correlation between TSO and whole brain atrophy rate ($R^2=0.11$, p=0.18) was found by the embodiment. Since study subjects were evaluated approximately every 2-3 years, TSO values form clusters separated by 2-3 years.

Statistical resampling aimed to account for the uncertainty in the Alzheimer's disease onset date confirmed these significance levels, with corrected p=0.008 for the left MTL, p=0.04 for the right MTL, and p=0.005 for the left and right MTL combined.

In order to compare more explicitly the contribution of the left versus right MTL, these variables were entered in permuted order using a two-block stepwise regression model. The addition of left MTL to the model containing right MTL increased $R^2$ by 0.256 (p=0.01). However, right MTL did not add significant predictive power when entered to the model containing left MTL. The paired samples t-test revealed a difference between the mean atrophy levels of the two brain sides (1.9%/year for right MTL versus 2.6%/year for the left MTL, p=0.05).

At the time of onset, atrophy rate of the entire brain was 1.4%/year, in the left MTL it was 2.2%/year, and in the right MTL 1.8%/year. There was no correlation between TSO and whole brain atrophy rate (FIG. 3, $R^2=0.11$, p=0.18). Neither age, gender, nor education level correlated with the atrophy rates (p>0.05).

A multivariate linear regression model was used to relate the TSO with the annual changes in MMSE and psychometric tests. After covarying for subject's age, gender, and education, stepwise addition of MMSE and psychometric test results yielded a linear model with $R^2=0.40$, p=0.130. Only the annual change in the immediate paired associates recall test scores correlated with the TSO (p=0.031). Nearly a third (32%) of Alzheimer's disease subjects were unable to complete the delayed shopping list recall and the visual recognition span tests and received a zero score. The paired associates recall test also showed a large "floor" effect, with 30% of Alzheimer's disease subjects receiving zero score at the baseline visit. In a three-step linear regression model TSO, a dependent variable, was expressed in terms of (a) the covariates: gender, education level, and age; (b) the annual change in MMSE and in all psychometric measures; and finally (c) the annual rates of atrophy in the left MTL, right MTL, and in the whole brain. The addition of neuroimaging measures resulted in an improvement ($R^2$ increase from 0.40 to 0.67, p=0.005) and identified the left MTL atrophy rate as the sole predictor of the TSO.

A normal control group consisted of 7 men and 14 women, aged 60-78, with mean age 67.8+/−5.2. The annual MTL atrophy rate (both left and right sides combined) in this group was 0.37+/−0.34%/year. There was no significant correlation between the rate of MTL atrophy and age, gender or education level of the control subjects.

A logistic regression analysis aimed at classifying the group membership (Alzheimer's disease versus normal control) based on the age, gender, education level, and MTL atrophy rate yielded a classification accuracy of 92.3%. Age, gender, and education did not significantly contribute to the logistic model. Only one control subject and two Alzheimer's disease patients were incorrectly classified. The two falsely classified Alzheimer's disease patients were imaged 2.8-2.9 years before the onset of Alzheimer's disease. MTL atrophy rate was the only significant variable in the logistic regression (p=0.02, odds ratio=1.6 for each 0.1% increase in MTL atrophy rate/year, 95% CI 1.1-2.2). When baseline atrophy was used instead the atrophy rate, the classification accuracy is reduced to 76.9%.

The increase in brain atrophy rates for longer TSO is likely due to the increased territory of the brain affected by the disease process. Pathologic staging of Alzheimer's disease proposes involvement of an increasingly large number of brain regions in successive stages of the disease. Annual brain loss will therefore increase even if cell death or shrinkage per unit volume proceeds at a steady rate. If this mechanism were correct, then the increase in atrophy rates will end when the entire brain becomes affected by the disease. Another, methodological explanation is based on the fact is that even with a steady course of volume loss $\Delta V = \text{const } \Delta t$, the atrophy rate $\Delta V/(\Delta t\, V)$ will appear to increase due to the reduction of the denominator V with disease duration.

It is of interest to analyze a model of linearly increasing atrophy rates seen in FIG. 6. If V(t) denotes the volume and V'(t) its derivative as a function of time t (also denoted as TSO), then the finding can be written as:

$$V'(t)/V(t) = kt + q,\ t > 0,\ V(0) = V_0,$$

where k is the slope and q the intercept of the regression line in FIG. 3. The solution of Eq. 1 is given by a bell shaped function, which for q=0 is simply $$V(t) = V_0 e^{-kt^2}$$

(If q is not ignored, the shape of V(t) does not change in a significant way.) The maximum value of V' occurs at the time $$t_{max} = 1/\sqrt{2k}$$

Since the value of k for left MTL was 0.0073/year², $t_{max} \approx 8$ years, a value that approximates an average time from the Alzheimer's disease diagnosis to death. Thus, the model is consistent with the premise of increasing territory affected by the disease and suggests that death from Alzheimer's disease tends to occur when the territorial spread is at its maximum.

Although the rate of MTL atrophy was measured using two MRI scans for each subject, a more direct evaluation of the relationship between the atrophy rate and the TSO would require comparing the brain at three or more times for each subject.

Study 2 demonstrates a positive linear correlation between the rate of atrophy within the MTL and the time since the clinical diagnosis of Alzheimer's disease. Subjects who had been diagnosed with Alzheimer's disease for a longer period showed a greater annual rate of atrophy, with an estimated overall 0.5% per year increase in the rate for each additional year the subject survives with Alzheimer's disease. Analysis indicates that the TSO, and not the age per se, correlates with this annual rise in the atrophy rate. A similar analysis of a control group of cognitively normal elderly confirms a small rate (averaging 0.3% per year) of MTL atrophy.

While the methods disclosed herein have been described and shown with reference to particular operations performed in a particular order, it will be understood that these operations may be combined, sub-divided, or re-ordered to form equivalent methods without departing from the teachings of the present invention. Accordingly, unless specifically indicated herein, the order and grouping of the operations is not a limitation of the present invention.

The methods and operations described herein may be carried out by any suitable computing and/or imaging devices. Such devices may be provided with appropriate software or hardware to configure the devices to perform the steps of the invention. For example, each of the various operations listed herein may be performed by a dedicated software module running on a computing device. Accordingly, the present invention is intended to embrace such apparatuses capable of performing the disclosed methods, as well as the methods themselves.

Additionally, exemplary source code for performing certain methods described herein is listed in Appendix A, attached hereto. Such source code is one example of the aforementioned software capable of operating on a computing device.

It should be noted that the applications of the disclosed invention are relatively far-reaching. For example, embodiments of the present invention provide for determining a change to a geometric structure. Embodiments of the present invention may be utilized to evaluate atrophy in human or animal anatomical structures, such as the brain, lungs, or other structures. Embodiments of the present invention may also be used to evaluate other changes in a structure's volume, so as to evaluate the growth or decay of tumors, or morphological changes such as shape (e.g. bump, bulge, etc) in a human or animal. The evaluation methods disclosed herein can be used to study or characterize various medical conditions, for example but not limited to, evaluation of brain atrophy, diagnosis of various medical conditions, evaluation of response to therapy, evaluation of disease progression, evaluation of new drug and therapeutic protocols, detection of onset of disease.

It should be appreciated that reference throughout this specification to "one embodiment" or "an embodiment" or "one example" or "an example" means that a particular feature, structure or characteristic described in connection with the embodiment may be included, if desired, in at least one embodiment of the present invention. Therefore, it should be appreciated that two or more references to "an embodiment" or "one embodiment" or "an alternative embodiment" or "one example" or "an example" in various portions of this specification are not necessarily all referring to the same embodiment.

While the present invention has been described in terms of specific embodiments thereof, it will be understood in view of the present disclosure, that numerous variations upon the invention are now enabled to those skilled in the art, which variations yet reside within the scope of the present teaching. Accordingly, the invention is to be broadly construed, and limited only by the scope and spirit of the claims now appended hereto.

APPENDIX A

```
/*********************************************************************
Border2.c computes the regional atrophy rate from a pair of MR scans
bas.im and fol.im. Bas.roi is a MIDAS file with four input ROIs:
      BORDER (default=0), INTER_BAS (def=1), INTER_FOL (def=2), INTER_BOTH (def=3)
(These ROIs are constructed by border1.c). Also given on input is a list
ROI1 ROI2 ... ROIN to be analyzed. For each of those, border2.c integrates
MR signal over the border region, normalizes it over the interior regions,
and computes the atrophy rate. option –w writes a normalized
partial difference image
```

APPENDIX A-continued

```
usage: border2 [-v 0/1 -f fst_sl -l lst_sl -c csf/brain1 -d csf/brain2 -o lo_clamp -h hi_clamp
               -O BO -1 I1 -2 I2 -i Iboth -w out.im] bas.im fol.im ROI1 ROI2 ...ROIN
*************************************************************************/
#include <stdio.h>
#include <math.h>
#include <string.h>
#include <stdlib.h>
#define MAXREG 20
#define MAXROI 31
int atoi( );          /* functions called */
void Usage(void);
int getheader( );
int getslice( );
int getkey( );
int cpheader( );
int putslice( );
void validate_roi(int roino, int BORDER, int INTER_BAS, int INTER_FOL, int INTER_BOTH);
void mkroiname(char *filename, char *roifile);
/* globals for Wai's IO ROI routines */
int nSlice, nPixel;
int cSlice;
extern unsigned long **roi;
unsigned long **AllocateRoi( );
void FreeRoi(unsigned long **roi);
int Q_SwapByte;
int FileError( char *error);
/* end IO ROI library globals */
main(argc, argv)
    int argc;
    char *argv[];
{
    char *ap, *basim, *folim, *outim; /* argument pointer */
    int iarg, nin; /* argument counter */
    /* variables for ROI codes are in CAPS */
    int BORDER=0, INTER_BAS=1, INTER_FOL=2, INTER_BOTH=3;
    double lo_clamp=0.2, hi_clamp=0.8;
    int verbose=1, write_border_shift, nreg, ROIN[MAXREG+1],
        fst_slice, lst_slice, i, j, x, y, slice, ipix;
    double csf_brain, csf_brainf, csfbas[MAXREG+1], csffol[MAXREG+1], idbas[MAXREG+1],
        idfol[MAXREG+1], frvoxbas, frvoxfol, n_intbas[MAXREG+1], n_roi[MAXREG+1],
        n_intfol[MAXREG+1], n_intboth[MAXREG+1], s_intbas[MAXREG+1],
        s_intfol[MAXREG+1], v_borbas[MAXREG+1], v_borfol[MAXREG+1];
    int xres, xres2,yres,yres2,zres,zres2,bpp,bpp2,chann,status; /* image header stuff */
    int short *inpix_bas, *inpix_fol, *outdiff;          /* pixel buffers */
char roiname[256];
unsigned long regbit[MAXREG+1], r, rbas, rfol, rboth, r0, intbasbit,
               intfolbit, intbothbit, borderbit;
double voxvol, pixsiz_bas, pixsiz_fol, sthick_bas, sthick_fol;
nin=0; /* counts input arguments (not flags) from 1 on
          since we need two volumes, nregs = nin-2 */
fst_slice= -1;
lst_slice= -1;
write_border_shift=0;
csf_brain = 0.36;
csf_brainf = csf_brain;
for (iarg = 1; iarg < argc; iarg++) {
    ap = argv[iarg]; /* get pointer to argument */
    if ((*(ap) == '-') && (*(ap + 1 ) == 'v') && (iarg + 1 < argc)) {
        iarg++;
        verbose = atoi(argv[iarg]);
        if (verbose) printf("verbose output\n");
    } else if ((*(ap) == '-') && (*(ap + 1) == 'l') && (iarg + 1 < argc)) {
        iarg++;
        lst_slice = atoi(argv[iarg]);
        if (verbose) printf("last slice = %d\n", lst_slice);
    } else if ((*(ap) == '-') && (*(ap + 1) == 'f') && (iarg + 1 < argc)) {
        iarg++;
        fst_slice = atoi(argv[iarg]);
        if (verbose) printf("first slice = %d\n", fst_slice);
    } else if ( (*(ap) == '-') && (*(ap + 1) == 'c') && (iarg + 1 < argc) ) {
        iarg++;
        csf_brain = atof(argv[iarg]);
        if (verbose) printf(" csf/brain contrast =%lf\n",csf_brain);
    } else if ( (*(ap) == '-') && (*(ap + 1) == 'w') && (iarg + 1 < argc) ) {
        iarg++;
        write_border_shift=1;
        outim = argv[iarg];
        if (verbose) printf(" writing border shift image to %s\n", outim);
```

APPENDIX A-continued

```
} else if ( (*(ap) == '-') && (*(ap + 1) == 'd') && (iarg + 1 < argc) ) {
    iarg++;
    csf_brainf = atof(argv[iarg]);
    if (verbose) printf(" csf/brain contrast at followup =%lf\n",csf_brainf);
} else if ( (*(ap) == '-') && (*(ap + 1) == '0') && (iarg + 1 < argc) ) {
    iarg++;
    BORDER = atoi(argv[iarg]);
    if (verbose) printf(" BORDER roi =%d\n",BORDER);
} else if ( (*(ap) == '-') && (*(ap + 1) == '1') && (iarg + 1 < argc) ) {
    iarg++;
    INTER_BAS = atoi(argv[iarg]);
    if (verbose) printf(" INTER_BAS roi =%d\n",INTER_BAS);
} else if ( (*(ap) == '-') && (*(ap + 1) == '2') && (iarg + 1 < argc) ) {
    iarg++;
    INTER_FOL = atoi(argv[iarg]);
    if (verbose) printf(" INTER_FOL roi =%d\n",INTER_FOL);
} else if ( (*(ap) == '-') && (*(ap + 1) == 'i') && (iarg + 1 < argc) ) {
    iarg++;
    INTER_BOTH = atoi(argv[iarg]);
    if (verbose) printf(" INTER_BOTH roi =%d\n",INTER_BOTH);
} else if ( (*(ap) == '-') && (*(ap + 1) == 'o') && (iarg + 1 < argc) ) {
    iarg++;
    lo_clamp = atof(argv[iarg]);
    if (verbose) printf(" low clamp =%lf\n",lo_clamp);
} else if ( (*(ap) == '-') && (*(ap + 1) == 'h') && (iarg + 1 < argc) ) {
        iarg++;
        hi_clamp = atof(argv[iarg]);
        if (verbose) printf(" high clamp =%lf\n", hi_clamp);
} else if (*(ap) == '-') { /* bad flag */
    Usage( );
} else {
    nin++;
    if (nin == 1)
        basim=ap;
    else if (nin == 2)
        folim=ap;
    else if (nin-2 <= MAXREG)
        ROIN[nin-2] = atoi(ap);
    }
} /* for iarg */
/* validate input parameters */
nreg=nin-2;
if (nreg<1 || nreg>MAXREG) Usage( );
if (verbose) printf("%s\n", basim);
for(i=1; i<=nreg; i++)
    validate_roi(ROIN[i],BORDER,INTER_BAS,INTER_FOL,INTER_BOTH);
/* open bas.im file, read its header */
if ((status=getheader(basim,&bpp,&zres,&xres,&yres,&chann)) != 0) {
    printf("border: getheader: error %d file %s\n",status,basim);
    exit(-1);
    }
/* open fol.im, read & compare headers */
if ((status=getheader(folim,&bpp2,&zres2,&xres2,&yres2,&chann)) != 0) {
    printf("border: getheader: error %d file %s\n",status,folim);
    exit(-1);
    }
if (zres2 != zres || xres2 != xres || yres2 != yres || xres != yres ) {
    printf("border: invalid resolution, xres %d xres2 %d yres %d yres2 %d\n",
        xres,xres2,yres,yres2);
    exit(-1);
    }
if (getkey(basim,"Pixel size",&pixsiz_bas) != 0) pixsiz_bas=1.0;
if (getkey(folim,"Pixel size",&pixsiz_fol) != 0) pixsiz_fol=1.0;
if (getkey(basim,"Slice width",&sthick_bas) != 0) sthick_bas=1.0;
if (getkey(folim,"Slice width",&sthick_fol) != 0) sthick_fol=1.0;
if (pixsiz_bas != pixsiz_fol || sthick_bas != sthick_fol) {
    printf("border: voxel mismatch, bas: pixsiz=%lf thick=%lf fol: pixsiz=%lf thick=%lf\n",
        pixsiz_bas,pixsiz_fol,sthick_bas,sthick_fol);
    exit(-1);
    }
voxvol=pixsiz_bas*pixsiz_bas*sthick_bas;
if (verbose) {
                printf("voxel volume: %8.2lf mm3\n",voxvol);
            };
/* fst_slice, lst_slice */
if (fst_slice == -1 ) fst_slice=1;
```

APPENDIX A-continued

```
    if (lst_slice == -1) lst_slice= zres;
    if (fst_slice <1 || lst_slice>zres || fst_slice>lst_slice ) {
        printf("border: invalid slice range, fst_slice %d lst_slice %d zres %d\n",
                fst_slice, lst_slice,zres);
        exit(-1);
    }
    if (csf_brain <= 0.05 || csf_brain >= 0.95 ) {
        printf("border: invalid csf/brain contrast %lf\n",csf_brain);
        exit(-1);
    }
    if (csf_brainf < 0.05 || csf_brainf > 0.95) {
        printf("border: invalid csf/brain contrast at followup %lf\n",csf_brainf);
        exit(-1);
    }
    if (lo_clamp < 0. || lo_clamp>hi_clamp || hi_clamp > 1.) {
        printf("border: invalid low clamp or high clamp values: %lf %lf\n",lo_clamp,hi_clamp);
        exit(-1);
    }
    if (BORDER == INTER_BAS || BORDER==INTER_FOL || BORDER == INTER_BOTH ||
        INTER_BAS==INTER_FOL || INTER_BAS==INTER_BOTH ||
INTER_FOL==INTER_BOTH ){
        printf("border: duplicate border/interior ROI numbers %d %d %d %d\n",
                        BORDER,INTER_BAS,INTER_FOL,INTER_BOTH);
        exit(-1);
    }
    /*
    printf("fst_slice: %d\n",fst_slice);
    printf("lst_slice: %d\n",lst_slice);
    printf("csf_brain: %lf\n",csf_brain);
    printf("csf_brainf: %lf\n",csf_brainf);
    for(i=1; i<=nreg; i++)
      printf("region %d: %d\n",i,ROIN[i]);
    */
/* allocate buffers inpix_bas, inpix_fol for image data (1 slice)
    and buffer roi for ROI data (also 1 slice) */
if ( ( inpix_bas = (short *) malloc ( xres*yres*sizeof(short) )) == NULL ) {
    printf ( "border: can't malloc inpix_bas buffer\n" );
    exit (-1);
}
if ( ( inpix_fol = (short *) malloc ( xres*yres*sizeof(short) )) == NULL ) {
    printf ( "border: can't malloc inpix_fol buffer\n" );
    exit (-1);
}
/* allocate buffer outdiff for difference image */
if (write_border_shift) {
    if ( ( outdiff = (short *) malloc ( xres*yres*sizeof(short) )) == NULL ) {
        printf ( "border: can't malloc outdiff buffer\n" );
        exit (-1);
    }
}
/* pass 1. compute SI for interior brain regions, baseline image -> brain_bas[i]
                            followup image -> brain_fol[i] */
Q_SwapByte = CheckByteOrder( );
nSlice=zres; /* # of slices */
nPixel = xres; /* # of pixels must be 128/256 */
roi = AllocateRoi(nPixel);
mkroiname(basim, roiname);
        /* open ROI file and set bits in Roi position */
        if (!RoiIO( 0, roiname, nPixel)) {
            printf("can't open %s \n",roiname);
            exit(-1);
        }
    intbasbit = ( (unsigned long ) 1 << INTER_BAS );
    intfolbit = ( (unsigned long ) 1 << INTER_FOL );
    intbothbit = ( (unsigned long ) 1 << INTER_BOTH );
    for (i=1; i<=nreg; i++){
        regbit[i] = ( (unsigned long ) 1 << ROIN[i] );
        n_roi[i]=0.0;
        n_intbas[i]=0.0;
        n_intfol[i]=0.0;
        n_intboth[i]=0.0;
        s_intbas[i]=0.0;
        s_intfol[i]=0.0;
    }
    for ( slice=fst_slice; slice<=lst_slice; slice++ ) {
        /* read ROI for current slice into roi
            roi io library needs this global var cSlice */
        cSlice = slice-1;
        if ( !RoiIO(3) ) continue; /* skip to next slice */
        if ((status=getslice(basim,2,xres*yres,slice,inpix_bas)) !=0) {
```

APPENDIX A-continued

```
            printf("border: getslice: %s: error %d, slice %d\n",basim,status,slice);
            exit(-1);
        }
        if ((status=getslice(folim,2,xres*yres,slice,inpix_fol)) !=0) {
            printf("border: getslice: %s: error %d, slice %d\n",folim,status,slice);
            exit(-1);
        }
        /* process the slice, count and sum over interior regions */
        for( y=0; y<yres; y++)
        for( x=0; x<xres; x++) {
            ipix=y*xres+x;
            r = roi[y][x] ;
            rbas=r&intbasbit; rfol=r&intfolbit; rboth=r&intbothbit;
            for(i=1; i<=nreg; i++){
                r0= r®bit[i];
                if ( rbas && r0 ) {
                    n_intbas[i]++;
                    s_intbas[i] += inpix_bas[ipix];
                }
                if(rfol && r0) {
                    n_intfol[i]++;
                    s_intfol[i] += inpix_fol[ipix];
                }
                if ( rboth && r0) {
                    n_intboth[i]++;
                }
                if ( r0) {
                    n_roi[i]++;
                }
            }
        }
    } /* end first slice loop - computing interior signals */
    if (verbose ) {
        printf(" interior signal intensity size (pixels)\n");
        printf(" regions bas fol bas fol\n");
    }
    for(i=1; i<=nreg; i++) {
        if (n_intbas[i]==0) {
            printf("border: empty interior bas for roi=%d in %s\n",ROIN[i],roiname);
            exit(-1);
        }
        s_intbas[i] /= n_intbas[i];
        if (s_intbas[i]<=1.0) { /* we will divide by s_int[i] soon, check for zero */
            printf("border: interior bas too small, =%lf, for roi=%d in %s\n",s_intbas[i],i,roiname);
            exit(-1);
        }
        if (n_intfol[i]==0) {
            printf("border: empty interior fol for roi=%d in %s\n",ROIN[i],roiname);
            exit(-1);
        }
        s_intfol[i] /= n_intfol[i];
        if (s_intfol[i]<=1.0) { /* we will divide by s_int[i] soon, check for zero */
            printf("border: interior fol too small, =%lf, for roi=%d in %s\n",s_intfol[i],ROIN[i],roiname);
            exit(-1);
        }
        if (verbose) printf(" %3d %8.2lf %8.2lf %8.0lf %8.0lf\n",
                ROIN[i],s_intbas[i],s_intfol[i],n_intbas[i],n_intfol[i]);
    }
    if (verbose) printf("\n");
    /* pass 2 - compute volumes of the brain at baseline and followup */
    borderbit = ( (unsigned long ) 1 << BORDER );
    for(i=1; i<=nreg; i++){
        v_borbas[i]=0.0;
        v_borfol[i]=0.0;
        csfbas[i] = s_intbas[i]*csf_brain;
        csffol[i] = s_intfol[i]*csf_brainf;
        idbas[i] = 1.0/ (s_intbas[i]*(1.0-csf_brain));
        idfol[i] = 1.0/ (s_intfol[i]*(1.0-csf_brainf));
    }
    if (write_border_shift) { /* write zeros for slices out of selected range */
                for(i=0;i<(xres*yres);i++)
                        outdiff[i] = 0;
        for ( slice=1; slice<=zres; slice++ ) {
            if (slice>=fst_slice && slice <=lst_slice) continue;
                        if ((putslice(outim,bpp,xres*yres,slice,outdiff)) != 0) {
                    printf("border: can't write image %s slice: %d\n",outim,slice);
                    exit(-1);
                }
        } /* for slice */
    } /* if write */
```

APPENDIX A-continued

```
for ( slice=fst_slice; slice<=lst_slice; slice++ ) {
    /* read ROI for current slice into roi
        roi io library needs this global var cSlice */
    cSlice = slice-1 ;
        /* initializes difference buffer */
        if (write_border_shift) for(i=0;i<(xres*yres);i++) outdiff[i] = 0;
    if ( !RoiIO(3) ) { /* if NO ROI's on this slice */
        if (write_border_shift) {
                if ((putslice(outim,bpp,xres*yres,slice,outdiff)) != 0) {
                        printf("border: can't write image %s slice: %d\n",outim, slice);
                        exit(-1 );
                        }
                }
                continue; /* skip to next slice */
        }
    if ((status=getslice(basim,2,xres*yres,slice,inpix_bas)) !=0) {
        printf("border: getslice: %s: error %d, slice %d\n",basim.status.slice);
        exit(-1);
        }
    if ((status=getslice(folim,2,xres*yres,slice,inpix_fol)) !=0) {
        printf("border: getslice: %s: error %d, slice %d\n",folim,status,slice);
        exit(-1);
        }
    /* process the slice, count fractional pixel volume over border regions */
    for( y=0; y<yres; y++)
    for( x=0; x<xres; x++) {
        ipix=y*xres+x;
        r=roi[y][x];
        if (! (r&borderbit) ) continue;
        for (i=1; i<=nreg; i++){
            if ( ! (r®bit[i])) continue;
            frvoxbas = ( (double) inpix_bas[ipix]-csfbas[i]) * idbas[i];
            if (frvoxbas<lo_clamp) frvoxbas=0.0;
            else if (frvoxbas>hi_clamp) frvoxbas=1.0;
            v_borbas[i] += frvoxbas;
            frvoxfol = ( (double) inpix_fol[ipix]-csffol[i]) * idfol[i];
            if (frvoxfol<lo_clamp) frvoxfol=0;
            else if (frvoxfol>hi_clamp) frvoxfol=1.0;
            v_borfol[i] += frvoxfol;
            if (write_border_shift) { /* compute image difference */
                        outdiff[ipix] = 1000*(frvoxbas-frvoxfol);
                        }
            /* printf("%5d %5d %5d %8.2lf %7.5lf %8.2lf %7.5lf\n",
            y,x,i,(double) inpix_bas[ipix], frvoxbas ,(double) inpix_fol[ipix], frvoxfol);*/
            } /* for i <= nreg */
        } /* for y,x */
    if (write_border_shift) { /* write image difference */
        if ((putslice(outim,bpp,xres*yres,slice,outdiff)) != 0) {
                            printf("border: can't write image %s slice: %d\n",outim,slice);
                            exit(-1);
                        }
                }
    } /* end second slice loop - */
    if (write_border_shift) { /* write header image difference */
        if(cpheader(basim,outim,bpp,zres,xres,yres,chann) != 0) {
                printf("border: can't copy input header file: %s\n",basim);
                exit(1);
            }
    }
    if (verbose) {
            printf("          volumes (mm3)      atrophy\n");
            printf(" region total roi brain bas brain fol        rate (%%)\n");
            for(i=1; i<=nreg; i++){
                printf(" %3d %8.1lf %8.1lf %8.1lf %8.3lf\n",
                    ROIN[i], voxvol*n_roi[i], voxvol*(v_borbas[i]+n_intboth[i]),
                    voxvol*(v_borfol[i]+n_intboth[i]),
                    100.0*(v_borbas[i]-v_borfol[i])/(v_borbas[i]+n_intboth[i]) ) ;
                }
        } /* if verbose */
    for(i=1; i<=nreg; i++) printf(" %8.3lf",100.0*(v_borbas[i]-v_borfol[i])/(v_borbas[i]+n_intboth[i])
) ;
    printf("\n");
}
void Usage(void) {
        printf("usage: border2 bas.im fol.im ROI1 ... ROIN\n");
        printf("option(default): -c csf/brain <0.36> -d csf/brain @follow-up (0.36)\n");
        printf("         -o low_clamp (0.2) -h high_clamp (0.8)\n");
        printf("         -0 BORDER (0) -1 INTER_BAS (1) -2 INTER_FOL (2) -i
INTER_BOTH\n");
        printf("         -v 0/1 -f fst_sl -l lst_sl -w shift_image\n");
```

APPENDIX A-continued

```
        exit(-1);
    }
}
/*********************************************************************
validate_roi check if roi code is valid
*********************************************************************/
void validate_roi( int nroi, int BO, int IN1, int IN2, int INboth) {
    if (nroi==BO || nroi==IN1 || nroi==IN2 || nroi==INboth || nroi<0 || nroi>MAXROI) {
        printf("border: %d is invalid roi number\n",nroi);
        exit(-1);
    }
}
/*********************************************************************
mkroiname constructs roi filename from image filename
*********************************************************************/
void mkroiname(filename,roifile)
char *filename, *roifile;
{
    strcpy(roifile,filename);
    /* if it ends with .im, change it to .roi */
    if (strncmp(roifile+strlen(roifile)-3,".im",3)==0) {
        roifile[strlen(roifile)-3]=0;
        strcat(roifile,".roi");
    }
    /* if it ends with .hd, change it to .roi */
    else if (strncmp(roifile+strlen(roifile)-3,".hd",3)==0) {
        roifile[strlen(roifile)-3]=0;
        strcat(roifile,".roi");
    }
    else /* if it doesn't end with .roi, append .roi */
    if (strncmp(roifile+strlen(roifile)-4,".roi",4)!=0)
        strcat(roifile,".roi");
} /* mkroiname */
```

The invention claimed is:

1. A method for determining a change in at least one portion of a biological object, comprising:
    obtaining a first three-dimensional image and a second three-dimensional image of the object;
    determining a first region of interest within at least one of the first three-dimensional image or the second three-dimensional image;
    determining a second region of interest within another one of the first three-dimensional image or the second three-dimensional image, wherein the first and second regions have voxels therein;
    using a computer arrangement, normalizing the first region of interest by determining a normalization factor, and adjusting a signal associated with one of the first image or the second image by the normalization factor; and
    determining the change in the at least one portion by comparing the normalized first region of interest to the second region of interest.

2. The method of claim 1, further comprising the operation of segmenting the first region of interest.

3. The method of claim 1, wherein the operation of normalizing the first region of interest comprises:
    determining a difference in a value between the first region of interest and the second region of interest; and
    adjusting the value of the first region of interest accordingly.

4. The method of claim 3, wherein the value is selected from at least one of a signal intensity or contrast.

5. The method of claim 3, wherein the operation of normalizing the first region of interest is carried out without reference to a portion of the at least one of the first three-dimensional image or the second three-dimensional image outside the region of interest.

6. The method of claim 1, wherein:
    the first region of interest is determined within the first image;
    the second region of interest is determined within the second image; and
    the first and second regions of interest correspond when the first and second images are coregistered.

7. The method of claim 1, wherein the operation of adjusting the signal associated with one of the first image or the second image is applied only across the first region of interest.

8. The method of claim 6, further comprising the operations of:
    computing a first partial volume for the first region of interest;
    computing a second partial volume for the second region of interest; and
    determining the change between the first and second partial volumes.

9. The method of claim 8, further comprising the operations of:
    reducing a first noise associated with the first partial volume prior to determining the change between the first and second partial volumes; and
    reducing a second noise associated with the second partial volume prior to determining the change between the first and second partial volumes.

10. A non-transitory computer-readable medium containing computer-executable instructions for determining a change in at least one portion of a biological object which, when executed by a hardware processing arrangement, configure the hardware processing arrangement to perform procedures comprising:
    obtaining a first three-dimensional image and a second three-dimensional image of the object;
    determining a first region of interest within at least one of the first three-dimensional image or the second three-dimensional image;
    determining a second region of interest within another one of the first three-dimensional image or the second three-dimensional image, wherein the first and second regions have voxels therein;
    normalizing the first region of interest;
    determining the change in the at least one portion by comparing the normalized first region of interest to the second region of interest;

computing a first partial volume for the first region of interest;

computing a second partial volume for the second region of interest;

determining the change between the first and second partial volumes;

reducing a first noise associated with the first partial volume prior to determining the change between the first and second partial volumes; and reducing a second noise associated with the second partial volume prior to determining the change between the first and second partial volumes.

11. A non-transitory computer-readable medium containing computer-executable instructions for determining a change in at least one portion of a biological object which, when executed by a hardware processing arrangement, configure the hardware processing arrangement to perform procedures comprising:

obtaining a first three-dimensional image and a second three-dimensional image of the object;

determining a first region of interest within at least one of the first three-dimensional image or the second three-dimensional image;

determining a second region of interest within another one of the first three-dimensional image or the second three-dimensional image, wherein the first and second regions have voxels therein;

normalizing the first region of interest by determining a normalization factor, and adjusting a signal associated with one of the first image or the second image by the normalization factor; and determining the change in the at least one portion by comparing the normalized first region of interest to the second region of interest.

12. The method of claim 1, further comprising the operations of:

determining a first voxel set contained within the first region of interest;

determining a second voxel set contained within the second region of interest;

operating on the first voxel set and second voxel set to produce a third voxel set;

operating on the first voxel set and second voxel set to produce a fourth voxel set; and operating on the third voxel set and fourth voxel set to produce a border for the region of interest.

13. The method of claim 12, wherein the operation of operating on the first voxel set and second voxel set to produce a third voxel set comprises:

determining a set union of the first and second voxel sets; and inflating the set union to yield the third voxel set.

14. The method of claim 12, wherein the operation of operating on the first voxel set and second voxel set to produce a fourth voxel set comprises:

determining a set intersection of the first and second voxel sets; and eroding the set intersection to yield the fourth voxel set.

15. An apparatus for determining a change in at least one portion of a biological object, comprising:

at least one hardware processing arrangement which is configured to:

obtain a first three-dimensional image and a second three-dimensional image of the object, determine a first region of interest within at least one of the first three-dimensional image or the second three-dimensional image, determine a second region of interest within another one of the first three-dimensional image or the second three-dimensional image, wherein the first and second regions have voxels therein, normalize the first region of interest by determining a normalization factor, and adjusting a signal associated with one of the first image or the second image by the normalization factor, and determine the change in the at least one portion by comparing the normalized first region of interest to the second region of interest.

16. A method for determining a volume change between a first acquired three-dimensional image and a second acquired three-dimensional image associated with a biological object, comprising:

calculating a normalization factor for a first region of interest defined in the first acquired three-dimensional image, wherein the first region has first voxels therein;

adjusting a signal strength of the acquired three-dimensional second image by applying the normalization factor thereto;

computing a first partial volume for the first region of interest;

computing a second partial volume for a second region of interest defined in the second image, wherein the second region has second voxels therein; and using a hardware processing arrangement, determining a change in volume between the first and second partial volumes, wherein the operations performed on the first and second regions of interest are not performed on any other portion of the first or second images.

17. The method of claim 16, wherein the operation of calculating the normalization factor for the first region of interest comprises:

determining a first average signal intensity of an interior of the first region of interest;

determining a second average signal intensity of an interior of the second region of interest; and setting the normalization factor to equal the first average signal intensity divided by the second average signal intensity.

18. The method of claim 17, wherein the second region of interest comprises a group of voxels, and the adjusting procedure comprises scaling a signal intensity for each voxel within the group of voxels by the normalization factor.

19. A method for determining a change in a hippocampus of a brain, comprising:

obtaining a first three-dimensional image and a second three-dimensional image of the brain;

determining a first region of interest within at least one of the first and second three-dimensional images, the first region of interest including first voxels therein and encompassing the hippocampus;

determining a second region of interest within the other of the first and second three-dimensional images, the second region of interest including second voxels therein and encompassing the hippocampus;

normalizing the first region of interest by determining a normalization factor, and adjusting a signal associated with one of the first image or the second image by the normalization factor; and determining the change in hippocampus by comparing the normalized first region of interest to the second region of interest.

20. The method according to claim 19, wherein the operations performed on the first and second regions of interest are not performed on any other portion of the first or second images.

21. A non-transitory computer-readable medium containing computer-executable instructions for determining a volume change between a first acquired three-dimensional image and a second acquired three-dimensional image associated with a biological object which, when executed by a hardware processing arrangement, configure the hardware processing arrangement to perform procedures comprising:

calculating a normalization factor for a first region of interest defined in the first acquired three-dimensional image, wherein the first region has first voxels therein;
adjusting a signal strength of the second acquired three-dimensional image by applying the normalization factor thereto;
computing a first partial volume for the first region of interest;
computing a second partial volume for a second region of interest defined in the second image, wherein the second region has second voxels therein; and
determining a change in volume between the first and second partial volumes, wherein the operations performed on the first and second regions of interest are not performed on any other portion of the first or second images.

22. A non-transitory computer-readable medium containing computer-executable instructions for determining a change in a hippocampus of a brain which, when executed by a hardware processing arrangement, configure the hardware processing arrangement to perform procedures comprising:
obtaining a first three-dimensional image and a second three-dimensional image of the brain;
determining a first region of interest within at least one of the first and second three-dimensional images, the first region of interest including first voxel therein and encompassing the hippocampus;
determining a second region of interest within the other of the first and second three-dimensional images, the second region of interest including second voxel therein and encompassing the hippocampus;
normalizing the first region of interest; and
determining the change in hippocampus by comparing the normalized first region of interest to the second region of interest.

23. The method of claim 16, further comprising at least one of displaying or storing data associated with the change in volume in a storage arrangement in at least one of a user-accessible format or a user-readable format.

24. The computer-readable medium of claim 11, wherein, when the hardware processing arrangement executes the software instructions, the hardware processing arrangement is further configured to perform procedures comprising:
computing a first partial volume for each of a plurality of voxels associated with a first border of the first region of interest;
computing a second partial volume for each of a plurality of voxels associated with a second border of the second region of interest; and
further determining the change as a function of the first partial volume and the second partial volume.

25. The computer-readable medium of claim 24, wherein at least one of (i) the first partial volume is provided as a function of a first signal intensity of a first set of voxels associated with an interior of the first region of interest, or (ii) the second partial volume is provided as a function of a second signal intensity of a second set of voxels associated with an interior of the second region of interest.

26. The computer-readable medium of claim 25, wherein at least one of (i) the first signal intensity is provided as a function of a first average signal intensity of the first set of voxels, or (ii) the second signal intensity is provided as a function of an average signal intensity of the second set voxels.

27. The computer-readable medium of claim 26, wherein at least one of (i) the first signal intensity is provided as a further function of a contrast between the first signal intensity and a third signal intensity of a third set of voxels associated with a background, or (ii) the second signal intensity is provided as a further function of a contrast between the second signal intensity and the third signal intensity.

28. The computer-readable medium of claim 24, wherein the change is based on a difference between the first partial volume and the second partial volume.

29. The computer-readable medium of claim 21, wherein the computing the first partial volume comprises computing a partial volume for each of a plurality of voxels associated with a first border of the first region of interest, and the computing the second partial volume comprises computing a partial volume for each of a plurality of voxels associated with a second border of the second region of interest.

30. The computer-readable medium of claim 29, wherein at least one of (i) the first partial volume is provided as a function of a first signal intensity of a first set of voxels associated with an interior of the first region of interest, or (ii) the second partial volume is provided as a function of a second signal intensity of a second set of voxels associated with an interior of the second region of interest.

31. The computer-readable medium of claim 30, wherein at least one of (i) the first signal intensity is provided as a function of a first average signal intensity of the first set of voxels, or (ii) the second signal intensity is provided as a function of an average signal intensity of the second set voxels.

32. The computer-readable medium of claim 31, wherein at least one of (i) the first signal intensity is provided as a further function of a contrast between the first signal intensity and a third signal intensity of a third set of voxels associated with a background, or (ii) the second signal intensity is provided as a further function of a contrast between the second signal intensity and the third signal intensity.

33. The computer-readable medium of claim 29, wherein the change is based on a difference between the first partial volume and the second partial volume.

34. The apparatus of claim 15, wherein the hardware processing arrangement is further configured to:
compute a first partial volume for each of a plurality of voxels associated with a first border of the first region of interest, wherein the first partial volume is a function of a first signal intensity of a first set of voxels associated with an interior of the first region of interest, and wherein the first signal intensity is provided as a function of a first average signal intensity of the first set of voxels, and a contrast between the first signal intensity and a third signal intensity of a third set of voxels associated with a background;
compute a second partial volume for each of a plurality of voxels associated with a second border of the second region of interest, wherein the second partial volume is provided as a function of a second signal intensity of a second set of voxels associated with an interior of the second region of interest, and wherein the second signal intensity is provided as a function of an average signal intensity of the second set voxels, and a contrast between the second signal intensity and the third signal intensity; and
further determine the change as a function of the first partial volume and the second partial volume, wherein the change is based on a difference between the first partial volume and the second partial volume.

35. The method of claim 17, wherein (i) the computing the first partial volume comprises computing a partial volume for each of a plurality of voxels associated with a first border of the first region of interest as a function of the first average signal intensity and a contrast between the first average signal intensity and a further signal intensity of a further set of voxels associated with a background, (ii) the computing the second partial volume comprises computing a partial volume for each of a plurality of voxels associated with a second border of the second region of interest as a function of the second average signal intensity and a contrast between the second average signal intensity and the further signal intensity, and (iii) the change is based on a difference between the first partial volume and the second partial volume.

36. A non-transitory computer-readable medium containing computer-executable instructions for determining a change in at least one portion of a biological object which, when executed by a hardware processing arrangement, configure the hardware processing arrangement to perform procedures comprising:
   obtaining a first three-dimensional image and a second three-dimensional image of the object;
   determining a first voxel set comprising voxels associated with a first region of interest defined in the first image;
   determining a second voxel set comprising voxels associated with a second region of interest defined in the second image;
   operating on the first voxel set to obtain a first interior voxel set;
   operating on the second voxel set to obtain a second interior voxel set;
   operating on the first voxel set to obtain a first border voxel set;
   operating on the second voxel set to obtain a second border voxel set;
   computing a first partial volume for the first border voxel set as function of at least one of (i) a first signal intensity of the first interior voxel set, or (ii) a further signal intensity of voxels associated with a background;
   computing a second partial volume for the second border voxel set as function of at least one of (i) a second signal intensity of the second interior voxel set, or (ii) the further signal intensity; and
   determining a change between the first partial volume and the second partial volume.

37. The computer-readable medium of claim 36, wherein, when the hardware processing arrangement executes the software instructions, the hardware processing arrangement is further configured to perform procedures comprising:
   calculating at least one of (i) a first normalization factor for the first region of interest, or (ii) a second normalization factor for the second region of interest; and
   adjusting at least one of (i) a first signal strength of the first voxel set based on the first normalization factor, or (ii) a second signal strength of the second voxel set based on the second normalization factor.

38. The computer-readable medium of claim 36, wherein at least one of the first interior voxel set or the second interior voxel set is obtained by at least one of (i) determining a first set intersection of the first and second voxels sets, and eroding the first set intersection, or (ii) eroding the first and second voxels sets, and determining a second set intersection of the eroded first and second voxels sets.

39. The computer-readable medium of claim 36, wherein at least one of the first border voxel set or the second border voxel set is obtained by at least one of (i) determining a set union of the first and second voxel sets, (ii) inflating the set union, or (iii) determining a difference between the inflated set union and an interior set associated with at least one of the first voxel set or the second voxel set.

40. A method for determining a change in at least one portion of a biological object, comprising:
   obtaining a first three-dimensional image and a second three-dimensional image of the object;
   determining a first region of interest within at least one of the first three-dimensional image or the second three-dimensional image;
   determining a second region of interest within another one of the first three-dimensional image or the second three-dimensional image, wherein the first and second regions have voxels therein;
   normalizing the first region of interest;
   determining the change in the at least one portion by comparing the normalized first region of interest to the second region of interest;
   using a computing arrangement, computing a first partial volume for the first region of interest;
   computing a second partial volume for the second region of interest;
   determining the change between the first and second partial volumes;
   reducing a first noise associated with the first partial volume prior to determining the change between the first and second partial volumes; and
   reducing a second noise associated with the second partial volume prior to determining the change between the first and second partial volumes.

41. A system for determining a change in at least one portion of a biological object, comprising:
   at least one hardware processing arrangement which is configured to:
      obtain a first three-dimensional image and a second three-dimensional image of the object;
      determine a first region of interest within at least one of the first three-dimensional image or the second three-dimensional image;
      determine a second region of interest within another one of the first three-dimensional image or the second three-dimensional image, wherein the first and second regions have voxels therein;
      normalize the first region of interest;
      determine the change in the at least one portion by comparing the normalized first region of interest to the second region of interest;
      compute a first partial volume for the first region of interest;
      compute a second partial volume for the second region of interest;
      determine the change between the first and second partial volumes;
      reduce a first noise associated with the first partial volume prior to determining the change between the first and second partial volumes; and
      reduce a second noise associated with the second partial volume prior to determining the change between the first and second partial volumes.

* * * * *